United States Patent
Shak

(10) Patent No.: US 7,297,526 B2
(45) Date of Patent: Nov. 20, 2007

(54) HUMAN DNASE

(75) Inventor: Steven Shak, Burlingame, CA (US)

(73) Assignee: Genentech, Inc., South San Francisco, CA (US)

(*) Notice: Subject to any disclaimer, the term of this patent is extended or adjusted under 35 U.S.C. 154(b) by 424 days.

(21) Appl. No.: 10/839,046

(22) Filed: May 4, 2004

(65) Prior Publication Data
US 2005/0009056 A1 Jan. 13, 2005

Related U.S. Application Data

(60) Continuation of application No. 10/005,675, filed on Nov. 7, 2001, now abandoned, which is a continuation of application No. 09/669,306, filed on Sep. 25, 2000, now abandoned, which is a continuation of application No. 08/761,578, filed on Dec. 9, 1996, now abandoned, which is a continuation of application No. 08/528,876, filed on Sep. 15, 1995, now abandoned, which is a continuation of application No. 08/117,584, filed on Sep. 3, 1993, now abandoned, which is a division of application No. 07/914,226, filed on Jul. 13, 1992, now abandoned, which is a continuation of application No. 07/448,038, filed on Dec. 8, 1989, now abandoned, which is a continuation-in-part of application No. 07/289,958, filed on Dec. 23, 1988, now abandoned.

(51) Int. Cl.
C12N 9/16 (2006.01)
C12N 15/00 (2006.01)
C12N 5/00 (2006.01)
C07H 21/24 (2006.01)
C12P 21/06 (2006.01)

(52) U.S. Cl. .................. 435/196; 536/23.2; 435/320.1; 435/325; 435/252.3; 435/69.1; 435/369

(58) Field of Classification Search ................ 435/196, 435/320.1, 325, 252.3, 69.1, 369; 536/23.2
See application file for complete search history.

(56) References Cited

U.S. PATENT DOCUMENTS

| | | | |
|---|---|---|---|
| 2,801,956 A | 8/1957 | Baumgarten et al. | |
| 2,834,710 A | 5/1958 | Baumgarten et al. | |
| 3,208,908 A | 9/1965 | Maxwell et al. | |
| 3,663,690 A | 5/1972 | Eichel et al. | |
| 4,065,355 A | 12/1977 | Khouw et al. | |
| 5,279,823 A | 1/1994 | Frenz et al. | |

FOREIGN PATENT DOCUMENTS

WO   WO 90/07572   *   7/1990

OTHER PUBLICATIONS

Rosenstreich D., et al, A Human Uridine-Derived Interleukin 1 Inhibitor. Homology with Deoxyribonuclease I, J. Exp. Med. Nov. 1988, 168, 1767-1779.*

Kishi K. et al, Genetic polymorphism of human urine deoxyribonuclease I, Hum. Genet., Feb. 1989, 81, 295—abstract.*

Andersson, H., "A double-blind randomized comparison of the effect and tolerance of varidase versus saline when instilled in the urinary bladder in patients with catheter problems" *J. Int. Med. Res.* 14(2):91-94 (1986).

Ayvazian et al., "The Use of Parenterally Administered Pancreatic Desoxyribonuclease as an Adjunct in the Treatment of Pulmonary Abscesses" *Am. Rev. of Tuberculosis and Pulmonary Diseases* 76(1):1-21 (Jul. 1957).

Bendig., "The Production of Foreign Proteins in Mammalian Cells." *Genetic Engineering.* 7:91-127 (1988).

Cliffton et al., "Pancreatic Deoxyribonuclease (Dornase) Aerosol in Treatment of Bronchopulmonary Complications and Tracheitis Sicca" *Cancer* 14(2):414-420 (Mar.-Apr. 1961).

Contreras et al., "Effect of Plastic Containers on Liquid Preservation of Human Granulocytes. I. With and Without Deoxyribonuclease and Hydrocortisone" *Transfusion* 20(5):519-530 (Sep.-Oct. 1980).

Deckert, T., "The immunogenicity of new insulins" *Diabetes* 34 (Supplement 2):94-96 (1985).

Doctor, V.M., "Studies on the Purification and Properties of Human Plasma Deoxyribonuclease I" *Archives of Biochem. and Biophysics* 103:286-290 (1963).

Farber et al., "Enzymatic Debridement" *J. of Thoracic Surgery* pp. 45-54 (1953).

Funakoshi et al., "Clinical Studies on Human Pancreatic Deoxyribonuclease I" *Japanese Society of Gastroenterology* 14(1):48-54 (Feb. 1979).

Funakoshi et al., "Purification and Properties of Human Pancreatic Deoxyribonuclease 1" *J. Biochem.* 82(6):1771-1777 (1977).

Funakoshi, Akihiro et al., "Purification and properties of human pancreatic deoxyribonuclease I" *Chemical Abstract* (Abstract only) 88(7):46840 (1978).

Graham et al., "Characteristics of a Human Cell Line Transformed by DNA from Human Adenovirus Type 5" *J. Gen. Virol.* 36:59-72 (1977).

Hoover *Remington's Pharmaceutical Sciences*, Mack Publishing Co. pp. 972-973 (1975).

Hubbard et al., "A Preliminary Study of Aerosolized Recombinant Human Deoxyribonuclease I in the Treatment of Cystic Fibrosis" *New England J. of Medicine* 326(12):812-815 (Mar. 19, 1992).

Ito et al., "Human Urine DNase I: Immunological Identity with Human Pancreatic DNase I, and Enzymic and Proteochemical Properties of the Enzyme" *J. Biochem.* 95(5):1399-1406 (1984).

Johnson et al., "The Intravenous Injection of Bovine Crystalline Pancreatic Desoxyribonuclease into Patients" *J. Clin. Invest.* 33:1670-1686 (1954).

Liao et al., "Bovine Pancreatic Deoxyribonuclease A" *Journal of Biological Chemistry* 248(4):1489-1495 (1973).

(Continued)

Primary Examiner—Tekchand Saidha
Assistant Examiner—Malgorzata A. Walicka
(74) Attorney, Agent, or Firm—David W. Evans

(57) ABSTRACT

DNA isolates coding for human DNase and methods of obtaining such DNA are provided, together with expression systems for recombinant production of human DNase useful in therapeutic or diagnostic compositions.

12 Claims, 18 Drawing Sheets

OTHER PUBLICATIONS

Liao, Ta-Hsiu, "Bovine Pancreatic Deoxyribonuclease D" *Journal of Biological Chemistry* 249:2354-2356 (1973).

Liao, Ta-Hsiu, "Multiple forms of deoxyribonuclease I" *Mol. and Cell. Biochem.* 34:15-22 (1981).

Lieberman, Jack, "Dornase Aerosol Effect on Sputum Viscosity in Cases of Cystic Fibrosis" *Journal of the American Medical Assn.* 205(5):114-115 (Jul. 29, 1968).

Lourenco et al., "Clinical Aerosols. II. Therapeutic Aerosols" *Arch. Intern. Med.* 142:2299-2308 (Dec. 1982).

Love et al., "The Relationship between Human Serum and Human Pancreatic DNase I" *J. of Biol. Chem.* 254(24):12588-12594 (Dec. 25, 1979).

*The Merck Index* (Abstract 2890), Budavari et al., Eleventh edition, Rahway, NJ:Merck & Co., Inc. pp. 457 (1989).

Murai et al., "Purification and Properties of Deoxyribonuclease from Human Urine" *Biochimica et Biophysica Acta* 517:186-194 (1978).

Murai et al., "Purification and Properties of Deoxyribonuclease II from Human Urine" *J. Biochem.* 87:1097-1103 (1980).

Nefsky et al., "Preparation of immobilized monomeric actin and its use in the isolation of protease-free and ribonuclease-free pancreatic deoxyribonuclease I" *European Journal of Biochemistry* 179:215-219 (1989).

Old & Primrose *Principles of Gene Manipulation: an introduction to genetic engineering* pp. 99-101 (Blackwell Scientific 1987).

Paudel et al., "Comparison of the Three Primary Structures of Deoxribonuclease Isolated from Bovine, Ovine, and Porcine Pancreas" *J. of Biol. Chem.* 261(34):16012-16017 (Dec. 5, 1986).

Paudel et al., "Purification, Characterization, and the Complete Amino Acid Sequence of Porcine Pancreatice Deoxyribonuclease" *J. of Biol. Chem.* 261(34):16006-16011 (Dec. 5, 1986).

Potter et al., "The Composition of Pulmonary Secretions from Patients With and Without Cystic Fibrosis" *Am. J. Dis. Child.* 100:493-495 (1960).

Quaas et al., "Expression of the chemically synthesized gene for ribonuclease T1 in *Escherichia coli* using a secretion cloning vector" *European Journal of Biochemistry* 173:617-622 (1988).

Raskin, Philip, "Bronchospasm After Inhalation of Pancreatic Dornase" *Am. Rev. of Respiratory Disease* 98:697-698 (1968).

Rosenstreich et al., "A Human Urine-Derived Interleukin 1 Inhibitor" *Journal of Experimental Medicine* (Abstract #55-131389 (A)) 168:1767-1779 (Nov. 1988).

Salnikow et al., "Bovine Pancreatic Deoxyribonucleases A and C" *J. of Biol. Chem.* 248(5):1499-1501 (Mar. 10, 1973).

Salomon et al., "Aerosols of Pancreatic Dornase in Bronchopulmonary Disease" *Annals of Allergy* pp. 71-79 (Jan.-Feb. 1954).

Sasada et al., "Secretion of human EGF and IgE in mammalian cells by recombinant DNA techniques: use of a IL-2 leader sequence" *Cell Struct. Funct.* 13(2):129-141 (1988).

Segal et al., "Pancreatic Dornase Aerosols in Bronchopulmonary Disease" *Annals N.Y. Acad. Sci.* 68:138-143 (1957).

Seiyaku, Amano, "Deoxyribonuclease I purification by contacting liq. contg. mammalian pancreas extract with DNA fixed on agaroseat pH 4-5 and eluting by raising ionic strength" *Dialog Information Services*, (Dialog Accession No. 002567012, WPI Acc. No. 80-85035C/198048) (1998).

Seiyaku, Amano, "Patent Abstracts of Japan (Derwent World Patent Index (WPI) Accession No. 80-85035C" *Abstract of JP 55-131389* (Abstract only) 5(4):C 38 (Oct. 13, 1980).

Shak et al., "Recombinant Human DNase I Reduces the Viscosity of Cystic Fibrosis Sputum" *Proc. Natl. Acad. Sci. USA* 87(23):9188-9192 (Dec. 1990).

Shields et al., "Cloning of part of the gene for bovine deoxyribonuclease I" *Biochemical Society Transactions* 16:195-196 (1988).

Suggs et al., "Use of Synthetic Oligonucleotides as Hybridization Probes: Isolation of Cloned cDNA Sequences for Human $\beta_2$-Microglobulin" *Proc. Natl. Acad. Sci. USA* 78(11):6613-6617 (Nov. 1981).

Takahara et al., "The ompA signal peptide directed secretion of staphylococcal nuclease A by *Escherichia coli*" *Journal of Biological Chemistry* 260(5):2670-2674 (1985).

Wang et al., "Preparation of Protease-free and Ribonuclease-free Pancreatic Deoxyribonuclease" *J. of Biol. Chem.* 253(20):7216-7219 (Oct. 25, 1978).

Whittaker et al., "Isolation and characterization of four adenovirus type 12-transformed human embryo kidney cell lines" *Molecular Cell Biology* 4(1):110-116 (1984).

Wilson et al., "Immunogenicity of highly purified bovine insulin: a comparison with conventional bovine and highly purified human insulins" *Diabetologia* 28(9):667-670 (1985).

Wroblewski et al., "Presence of Desoxyribonuclease Activity in Human Serum" *P.S.E.B.M.* 74:443-445 (1950).

Yeager, Jr., Henry, "Tracheobronchial Secretion" *Am. J. of Medicine* 50:493-509 (Apr. 1971).

\* cited by examiner

```
                 10         20         30         40         50
hDNase   LKIAAFNIQTFGETKMSNATLVSYIVQILSRYDIALVQEVRDSHLTAVGK
         ********.************ ****.*. **** *...****** ****
bDNase   LKIAAFNIRTFGETKMSNATLASYIVRIVRRYDIVLIEQVRDSHLVAVGK
                 10         20         30         40         50

60         70         80         90        100
hDNase   LLDNLNQDAPDTYHYVVSEPLGRNSYKERYLFVYRPDQVSAVDSYYYDDG
         *** **** *.********************..**..** .*.* ****
bDNase   LLDYLNQDDPNTYHYVVSEPLGRNSYKERYLFLFRPNKVSVLDTYQYDDG
                 60         70         80         90        100

110        120        130        140        150
hDNase   CEPCGNDTFNREPAIVRFFSRFTEVREFAIVPLHAAPGDRVAEIDALYDV
         **.****.*.****.*.* *. * *.*****.**.**.* ****..****
bDNase   CESCGNDSFSREPAVVKFSSHSTKVKEFAIVALHSAPSDAVAEINSLYDV
                110        120        130        140        150

160        170        180        190        200
hDNase   YLDVQEKWGLEDVMLMGDFNAGCSYVRPSQWSSIRLWTSPTFQWLIPDSA
         *****.** *.**********.**** .********.**.*********
bDNase   YLDVQQKWHLNDVMLMGDFNADCSYVTSSQWSSIRLRTSSTFQWLIPDSA
                160        170        180        190        200

210        220        230        240        250
hDNase   DTTATPTHCAYDRIVVAGMLLRGAVVPDSALPFNFQAAYGLSDQLAQAIS
         *****.*.********** **...** ** **.*********...* ***
bDNase   DTTATSTNCAYDRIVVAGSLLQSSVVGPSAAPFDFQAAYGLSNEMALAIS
                210        220        230        240        250

260
hDNase   DHYPVEVMLK
         ******* *
bDNase   DHYPVEVTLT
                260
```

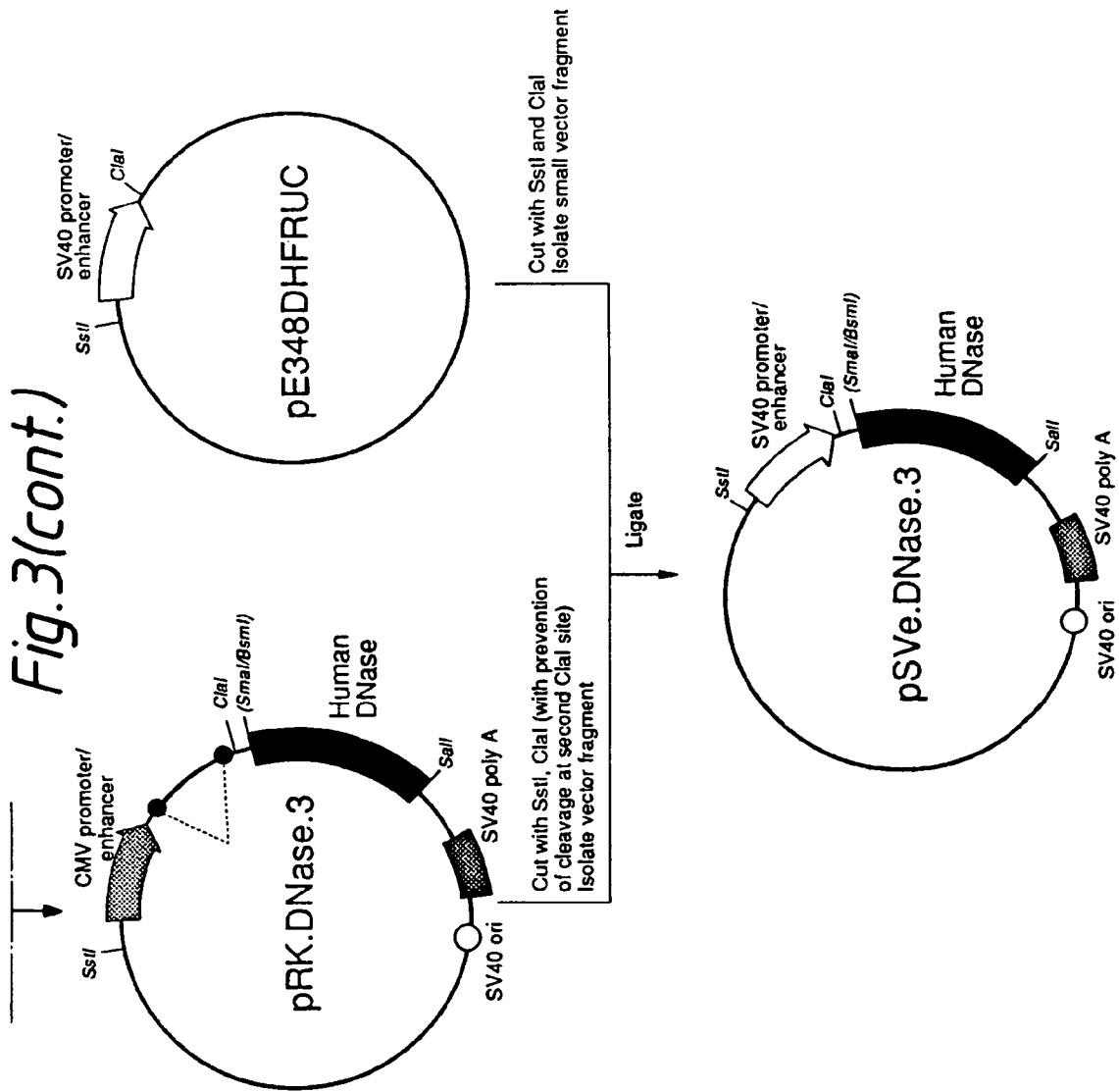

Fig. 6.

```
       aluI
       sstI
       sacI
       hgiJII
       hgiAI
       bsp1286
       banII
       taqI                                   taqI
                                              salI
                                              hindII
                                              hincII
                                              accI                           nlaIV
                                              pleI   aluI                    scrFI
                                              hinfI  pvuII                   ecoRII
  1  TTCGAGCTCG CCCGACATTG ATTATTGACT AGAGTCGACA GCTGTGGAAT GTGTGTCAGT TAGGGTGTGG AAAGTCCCCA GGCTCCCCAG CAGGCAGAAG
     AAGCTCGAGC GGGCTGTAAC TAATAACTGA TCTCAGCTGT CGACACCTTA CACACAGTCA ATCCCCACACC TTTCAGGGGT CCGAGGGGTC GTCCGTCTTC
               nsiI                                                                           sfaNI
               avaIII                              scrFI                                      nsiI
               nlaIII                              ecoRII                                     avaIII
               sphI sfaNI                          bstNI                                      nlaIII
               nspCIx                                                                         sphI
                                                                                              nspCIx
 101 TATGCAAAGC ATGCATCTCA ATTAGTCAGC AACCAGGTGT GGAAAGTCCC CAGGCTCCCC AGCAGGCAGA AGTATGCAAA GCATGCATCT CAATTAGTCA
     ATACGTTTCG TACGTAGAGT TAATCAGTCG TTGGTCCACA CCTTTCAGGG GTCCGAGGGG TCGTCCGTCT TCATACGTTT CGTACGTAGA GTTAATCAGT
                                       fokI                                    nlaIII
                                                                               styI
                                                                               ncoI
 201 GCAACCATAG TCCCGCCCCT AACTCCGCCC ATCCCCGCCC TAACTCCGCC CAGTTCCGCC CATTCTCCGC CCCATGGCTG ACTAATTTTT TTTATTTATG
     CGTTGGTATC AGGGCGGGGA TTGAGGCGGG TAGGGGCGGG ATTGAGGCGG GTCAAGGCGG GTAAGAGGCG GGGTACCGAC TGATTAAAAA AAATAAATAC
                                                            bsrI
              fnu4HI                                                                   styI                    scrFI
              bglI                                                                     avrII                   nciI
              sfiI     ddeI                                                            haeIII                  mspI
              haeIII haeIII                                                            stuI                    hpaII
              mnlI mnlI mnlI aluI                           mnlI                       haeI                    cauII
                                                                                       mnlI                    haeIII
 301 CAGAGGCCGA GGCCGCCTCG GCCTCTGAGC TATTCCAGAA GTAGTGAGGA GGCTTTTTTG GAGGCCTAGG CTTTTGCAAA AAGCTTATCG GGCCGGGAAC
     GTCTCCGGCT CCGGCGGAGC CGGAGACTCG ATAAGGTCTT CATCACTCCT CCGAAAAAAC CTCCGGATCC GAAAACGTTT TTCGAATAGC CCGGCCCTTG
                                                                                                aluI    sau96I
                                                                                                hindIII asuI
              hinfI                                          pleI                       bstXI
                                                             hinfI                      sau96I                fnu4HI
              thaI                                                                      haeIII                thaI
              fnuDII                                                                    asuI                  fnuDII
              bstUI                                rsaI                       styI                            bstUI     aseI
                                                                                                            sp6 promoter
 401 GGTGCATTGG AACGCGGATT CCCCGTGCCA AGAGTGACGT AAGTACCGCC TATAGAGTCT ATAGGCCCAC CCCCTTGGCT TGTTAGAAC GCGGCTACAA
     CCACGTAACC TTGCGCCTAA GGGGCACGGT TCTCACTGCA TTCATGGCGG ATATCTCAGA TATCCGGGTG GGGAACCGA AGCAATCTTG CGCCGATGTT
```

Fig.6(cont.)

```
                                                                                              sau96I
                                                                                              avaII
                                                                                              asuI
                                                                        hphI        sp6 RNA start    foKI                               scrFI
                                                                                                                                        ecoRII
     mseI                  note ATG                                                                                                     bstNI
501  TTAATACATA ACCTTATGTA TCATACACAT ACGATTAGG TGACACTATA GAATAACATC CACTTTGCCT TTCTCTCCAC AGGTGTCCAC TCCCAGGTCC
     AATTATGTAT TGGAATACAT AGTATGTGTA TGCTAAATCC ACTGTGATAT CTTATTGTAG GTGAAACGGA AAGAGAGGTG TCCACAGGTG AGGGTCCAGG
                                  bspMI
                         aluI     pstI
                         hindIII  fnu4HI
              mnlI  ddeI     bbvI                            mseI       hgaI
          cloning linker
1    AACTGCACCT CGGTTCTAAG CTTGGGCTGC AGGTCGCCGT GAATTAAGG GACGCTGTGA AGCA
     TTGACGTGGA GCCAAGATTC GAACCCGACG TCCAGCGGCA CTTAAATTCC CTGCGACACT TCGT
```

Fig. 7.

```
         aluI
         sstI
         sacI
         hgiJII
         hg1AI
         bsp1286
         banII                                         taqI
         taqI                                          salI
                                                      hindII
                                                      hincII                                              nlaIV
                                         pleI  aluI   accI                                                scrFI
                                         hinfI pvuII                                                      ecoRII
  1 TTCGAGCTCG CCCGACATTG ATTATTGACT AGAGTCGACA GCTGTGGAAT GTGTGTCAGT TAGGGTGTGG AAAGTCCCCA GGCTCCCCAG CAGGAGAAG
    AAGCTCGAGC GGGCTGTAAC TAATAACTGA TCTCAGCTGT CGACACCTTA CACACAGTCA ATCCCACACC TTTCAGGGGT CCGAGGGGTC GTCCGTCTTC sfaNI
            nsiI                                                                                      nsiI
            avaIII                                              scrFI                                 avaIII
            nlaIII                                              ecoRII                                nlaIII
            sphI sfaNI                                          bstNI                                 sphI
            nspCIx                                                                                    nspCIx
101 TATGCAAAGC ATGCATCTCA ATTAGTCAGC AACCAGGTGT GGAAAGTCCC GGCCTCCCCC AGCAGGCAGA AGTATGCAAA GCATGCATCT CAATTAGTCA
    ATACGTTTCG TACGTAGAGT TAATCAGTCG TTGGTCCACA CCTTTCAGGG CCGGAGGGGG TCGTCCGTCT TCATACGTTT CGTACGTAGA GTTAATCAGT nlaIII
                                            fokI                     bsrI               styI
                                                                                         ncoI
201 GCAACCATAG TCCCGCCCCT AACTCCGCGC ATCCCGCCCC TAGGGCGGGG ATTGAGGCGG GTCAAGGCGG CATTCTCCGC CCCATGGCTG ACTAATTTTT TTTATTTATG
    CGTTGGTATC AGGGCGGGGA TTGAGGCGCG TAGGGCGGGG ATCCCGCCCC TAACTCCGCC CAGTTCCGCC GTAAGAGGCG GGGTACCGAC TGATTAAAAA AAATAAATAC scrFI
                                                                                                                  ncil
                                                                                          styI                    mspI
                                                                                          avrII                   hpaII
                                                                                          haeIII                  haeIII
                                                                                          stuI                    xmaIII
                                                                                          haeI                    eagI
         fnu4HI                                            mnlI                                                   eaeI
         bglI                                              mnlI                                                   cfrI
         sfiI    ddeI                                                                                             aluI mspI cauII
         haeIII haeIII                                                                      GAGGCCTAGG CTTTTTGCAA hindIII hpaII
    mnlI mnlI    mnlI alui                                                                                        AAGCTTTATCC GGCCGGGAAC
301 CAGAGGCCGA GGCCGCCTCG GCCTCTGAGC TATTCCAGAA GTAGTGAGGA GGCTTTTTTG GAGGCCTAGG CTTTTTGCAA AGCTTTATCC GGCCGGGAAC
    GTCTCCGGCT CCGGCGGAGC CGGAGACTCG ATAAGGTCTT CATCACTCCT CCGAAAAAAC CTCCGGATCC GAAAACGTTT TCGAAATAGG CCGGCCCTTG fnu4HI
            hinfI                                                      bstXI
            thaI                                                       sau96I                               thaI
            fnuDII                           pleI                       haeIII                              fnuDII
            bstUI                  rsaI     hinfI                       asuI  styI                          bstUI         aseI
                                U1 matched splice donar                                   sp6 promoter
401 GGTGCATTGG AACGCGGATT CCCCGTGCCA AGTCAGT AGTACCGCC TATAGAGTCT AGGCCCTAGG CTCCGGATCC CCCCTTGGCT TCGTTAGAAC GCGGCTACAA CGCCGATGTT
    CCACGTAACC TTGCGCCTAA GGGGCACGGT TCAGTCA TCATGGCGG ATATCTCAGA TATCCGGGTG GGGAACCGA AGCAATCTTG CGCCGATGTT
```

Fig.7(cont.)

```
                                                                                                              sau96I
                                                                                                              avaII
                                                                                                              asuI
                                                                                                              scrFI
                                                                                                              ecoRII
                                                                            hphI          sp6 RNA start       bstNI
                 note ATG                                                                 fokI
     mseI
 501 TTAATACATA ACCTTATGTA TCATACACAT ACGATTAAGG TGACACTATA GAATAACATC CACTTTGCCT TTCTCTCCAC AGTGTCCAC TCCCAGTCC
     AATTATGTAT TGGAATACAT AGTATGTGTA TGCTAATTCC ACTGTGATAT CTTATTGTAG GTGAAACGGA AAGAGAGGTG TCCACAGGTG AGGGTCCAGG
                       aluI    bspMI
                       hindIII pstI
                  ddeI  fnu4HI
              mnlI       bbvI                             mseI     hgaI
          cloning linker
 601 AACTGCACCT CGGTTCTAAG CTTGGGCTGC AGGTCGCCCGT GAATTAAGG GACGCTGTGA AGCA
     TTGACGTGGA GCCAAGATTC GAACCCGACG TCCAGCGGCA CTTAAATTCC CTGCGACACT TCGT
   1
```

Fig. 8.

```
     aluI
     sstI
     sacI
     hgiJII
     hgiAI
     bsp1286
     banII
     taqI                                 taqI
                                          salI
                                          hindII
                                          hincII
                                          accI
                                          pleI    aluI
                                          hinfI   pvuII                                               scrFI
                                                                                                      ecoRII                          sfaNI
                                                                                                      bstNI              nlaIV       nsiI
   1 TTCGAGCTCG CCCGACATTG ATTATTGACT AGAGTCGACA GCTGTGGAAT GTGTGTCAGT TAGGGTGTGG AAAGTCCCCA GGCTCCCCAG CAGGCAGAAG
     AAGCTCGAGC GGGCTGTAAC TAATAACTGA TCTCAGCTGT CGACACCTTA CACACAGTCA ATCCCACACC TTTCAGGGGT CCGAGGGGTC GTCCGTCTTC avaIII
                 nsiI                                                                                                    nlaIII
                 avaIII                                                                                                  sphI
                 nlaIII                           scrFI                                                                  nspCIx
                 sphI sfaNI                       ecoRII                           AGCAGGCAGA AGTATGCAAA GCATGCATCT CAATTAGTCA
                 nspCIx                           bstNI
 101 TATGCAAAGC ATGCATCTCA ATTAGTCAGT AACCAGGTGT GGAAAGTCCC CAGGCCTCCCC AGCAGGCAGA AGTATGCAAA GCATGCATCT CAATTAGTCA
     ATACGTTTCG TACGTAGAGT TAATCAGTCA TTGGTCCACA CCTTTCAGGG GTCCGGAGGGG TCGTCCGTCT TCATACGTTT CGTACGTAGA GTTAATCAGT nlaIII
                                          fokI                                                   styI
                                                       bsrI                                      ncoI
 201 GCAACCATAG TCCCGCCCCT AACTCCGCCC ATCCCGCCCC TAACTCCGCC CAGTTCCGCC CATTCTCCGC CCCATGGCTG ACTAATTTTT TTTATTTATG
     CGTTGGTATC AGGGCGGGGA TTGAGGCGGG TAGGGCGGGG ATTGAGGCGG GTCAAGGCGG GTAAGAGGCG GGGTACCGAC TGATTAAAAA AAATAAATAC scrFI
                                                                                                                         nciI
                                                                        styI                                             mspI
                                                                        avrII                                            hpaII
                                                                        haeIII                                           haeIII
                         fnu4HI                                         stuI                                  xmaIII
                         bglI                                           hael                                  eagI
                         sfiI      ddeI                                 mnlI                                  eaeI
              haeIII haeIII                                             bstXI                                 cfrI
              mnlI mnlI mnlI alu I                                      sau96I                       aluI     mspI cauII
                 hinfI                          mnlI                    haeIII                       hindIII  hpaII
 301 CAGAGGCCGA GGCCCCCTCG GCCTCTGAGC TATTCCAGAA GTAGTGAGGA GGCTTTTTTG GAGGCCTAGG CTTTTGCAAA AAGCTTATCC GGCCGGGAAC
     GTCTCCGGCT CCGGGGGAGC CGGAGACTCG ATAAGGTCTT CATCACTCCT CCGAAAAAAC CTCCGGATCC GAAAACGTTT TTCGAATAGG CCGGCCCTTG thaI                              pleI                                                          fnu4HI
              fnuDII                            hinfI                                                         thaI
              bstUI                 rsaI                                                                      fnuDII
                         U1 matched splice donar                                                              bstUI       aseI
 401 GGTGCATTGG AACGGGGATT CCCCGTGCCA AGAGTCAGT AAGTACCGCC TATAGAGTCT ATAGGCCCAC CCCCTTGGCT TCGTTAGAAC GCGGCTACAA
     CCACGTAACC TTGCCCCTAA GGGGCACGGT TCATCAGTCA TTCATGGCGG ATATCTCAGA TATCCGGGTG GGGGAACCGA AGCAATCTTG CGCCGATGTT
                                                sp6 promoter
```

Fig.8(cont.)

```
                                                                                                                    aluI
                                                                                                                    hindIII
                                                                    sau96I                                     taqI
                                                                    avaII                                      bstBI
                                                                    asuI                                       asuII
                                                        scrFI                                             mnlI
                                                        ecoRII                                            cloning linker
                                                        bstNI
           sau3AI
           mboI
           dpnI
           alwI
           xhoII
           nlaIV
           bstYI
           bamHI
    mseI   alwI     removed ATG  lariat consensus           foKI
501 TTAATACATA ACCTTTTGGA TCCTATAGAC TGACATCCAC TTTGCCTTTC TCTCCACAGG TGTCCACTCC CAGGTCCAAC ·TGCACCTCGG TTCGAAGCTT
    AATTATGTAT TGGAAAACCT AGGATATCTG ACTGTAGGTG AAACGGAAAG AGAGGTGTCC ACAGGTGAGG GTCCAGGTTG ACGTGGAGCC AAGCTTCGAA
        bspMI
        pstI
        fnu4HI
        bbvI                msel    hgaI
  1 GGGCTGCAGG TCGCCGTGAA TTTAAGGGAC GCTGTGAAGC A
    CCCGACGTCC AGCGGCACTT AAATTCCCTG CGACACTTCG T
```

Fig. 9.

```
             aluI
             sstI                                          taqI
             sacI                                          salI
             hgiJII                                        hindII
             hgiAI                                         hincII
             bsp1286                                       accI
             banII                                         pleI     aluI
        taqI                                               hinfI    pvuII
    1 TTCGAGCTCG CCCGACATTG ATTATTGACT AGAGTCGACA GCTGTGGAAT GTGTGTCAGT
      AAGCTCGAGC GGGCTGTAAC TAATAACTGA TCTCAGCTGT CGACACCTTA CACACAGTCA nsiI
                              nlaIV                                avaIII
                        scrFI                                      nlaIII
                        ecoRII                                     sphI sfaNI
                        bstNI                                      nspCIx
   61 TAGGGTGTGG AAAGTCCCCA GGCTCCCCAG CAGGCAGAAG TATGCAAAGC ATGCATCTCA
      ATCCCACACC TTTCAGGGGT CCGAGGGGTC GTCCGTCTTC ATACGTTTCG TACGTAGAGT nlaIV
                   scrFI                    scrFI
                   ecoRII                   ecoRII
                   bstNI                    bstNI
  121 ATTAGTCAGC AACCAGGTGT GGAAAGTCCC CAGGCTCCCC AGCAGGCAGA AGTATGCAAA
      TAATCAGTCG TTGGTCCACA CCTTTCAGGG GTCCGAGGGG TCGTCCGTCT TCATACGTTT sfaNI
         nsiI
         avaIII
         nlaIII
         sphI
         nspCIx                                         fokI
  181 GCATGCATCT CAATTAGTCA GCAACCATAG TCCCGCCCCT AACTCCGCCC ATCCCGCCCC
      CGTACGTAGA GTTAATCAGT CGTTGGTATC AGGGCGGGGA TTGAGGCGGG TAGGGCGGGG nlaIII
                                              styI
                bsrI                          ncoI
  241 TAACTCCGCC CAGTTCCGCC CATTCTCCGC CCCATGGCTG ACTAATTTTT TTTATTTATG
      ATTGAGGCGG GTCAAGGCGG GTAAGAGGCG GGGTACCGAC TGATTAAAAA AAATAAATAC fnu4HI
                   bglI
                   sfiI          ddeI
             haeIII haeIII    haeIII                          mnlI
        mnlI  mnlI     mnlI      mnlI    aluI                 mnlI
  301 CAGAGGCCGA GGCCGCCTCG GCCTCTGAGC TATTCCAGAA GTAGTGAGGA GGCTTTTTTG
      GTCTCCGGCT CCGGCGGAGC CGGAGACTCG ATAAGGTCTT CATCACTCCT CCGAAAAAAC scrFI
                                            nciI
                                            mspI
                                            hpaII
                                            haeIII
             styI                           xmaIII
             avrII                          eagI
             haeIII                         eaeI                    hinfI
             stuI                           cfrI                    thaI
             haeI                 aluI      mspI  cauII             fnuDII
             mnlI                 hindIII   hpaII                   bstUI
  361 GAGGCCTAGG CTTTTGCAAA AAGCTTATCC GGCCGGGAAC GGTGCATTGG AACGCGGATT
      CTCCGGATCC GAAAACGTTT TTCGAATAGG CCGGCCCTTG CCACGTAACC TTGCGCCTAA bstXI
                                                      sau96I
                        pleI              pleI        haeIII
                        hinfI       rsaI  hinfI       asuI         styI
                        U1 matched splice donar
  421 CCCCGTGCCA AGAGTCAGGT AAGTACCGCC TATAGAGTCT ATAGGCCCAC CCCCTTGGCT
      GGGGCACGGT TCTCAGTCCA TTCATGGCGG ATATCTCAGA TATCCGGGTG GGGGAACCGA
```

Fig.9(cont.)

```
                                                       sau3AI
                                                       mboI
                                                       dpnI
                                                       alwI
                                                       xhoII
                                                       nlaIV
                                                       bstYI
                                                       bamHI
                                                       alwI
                                                       removed ATG
                                                            U2 match lariat consensus              thaI
          fnu4HI                                                                                   fnuDII
          thaI                                                                                     bstUI
          fnuDII      mseI                                                                         mnlI  nruI hindIII
          bstUI       aseI                                                                              cloning linker
    sp6 promoter
481 TCGTTAGAAC GCGGCTACAA TTAATACATA ACCTTTTGGA TCCTACTAAC TACTGACTTA
    AGCAATCTTG CGCCGATGTT AATTATGTAT TGGAAAACCT AGGATGATTG ATGACTGAAT
                                                 sau96I
                                                 avaII
                                                 asuI
                                                 scrFI
                                                 ecoRII
                                                 bstNI
541 TTCTTTTCCT TTCTCTCCAC AGGTGTCCAC TCCCAGGTCC AACTGCACCT CGGTTCGCGA
    AAGAAAAGGA AAGAGAGGTG TCCACAGGTG AGGGTCCAGG TTGACGTGGA GCCAAGCGCT
            bspMI
            pstI
            fnu4HI
    aluI    bbvI             mseI    hgaI
  1 AGCTTGGGCT GCAGGTCGCC GTGAATTTAA GGGACGCTGT GAAGCA
    TCGAACCCGA CGTCCAGCGG CACTTAAATT CCCTGCGACA CTTCGT
```

Fig. 10.

```
                                                               alu I
                                                               sst I
                                                               sac I
                                                               hgiJII
                                                               hgiAI
                                                               bsp1286
                                                               banII                  taq I
                                                               taq I                  sal I
                                                                                      hind II
                                                                                      hinc II
                                                                                      acc I                                                      nla IV
                                                               ple I    alu I
                                                               hinf I   pvu II                                                                   scrFI
                                                                                                                                                 ecoRII
                                                                                                                                                 bstNI
  1  TTCGAGCTCG  CCCGACATTG  ATTATTGACT  AGAGTCGACA  GCTGTGGAAT  GTGTGTCAGT  TAGGGTGTGG  AAAGTCCCCA  GGCTCCCCAG  CAGGCAGAAG
     AAGCTCGAGC  GGGCTGTAAC  TAATAACTGA  TCTCAGCTGT  CGACACCTTA  CACACAGTCA  ATCCCACACC  TTTCAGGGGT  CCGAGGGGTC  GTCCGTCTTC nsi I                                                                                       sfaN I
              ava III                                 scrFI                                               nsi I
              nla III                                 ecoRII                                              ava III
              sphI  sfaNI                             bstNI                                               nla III
              nspCIx                                                                                      sphI
                                                                                                          nspCIx
101  TATGCAAAGC  ATGCATCTCA  ATTAGTCAGC  AACCAGTGT   GGAAAGTCCC  CAGGCTCCCC  AGCAGGCAGA  AGTATGCAAA  GCATGCATCT  CAATTAGTCA
     ATACGTTTCG  TACGTAGAGT  TAATCAGTCG  TTGGTCCACA  CCTTTCAGGG  GTCCGAGGGG  TCGTCCGTCT  TCATACGTTT  CGTACGTAGA  GTTAATCAGT nla III
                              fok I                              bsr I                          sty I
                                                                                                nco I
201  GCAACCATAG  TCCCGCCCCT  AACTCCGCCC  ATCCCGGCCC  TAACTCCGCC  CAGTTCCGCC  CATTCTCCGC  CCCATGGCTG  ACTAATTTTT  TTTATTTATG
     CGTTGGTATC  AGGGCGGGGA  TTGAGGCGGG  TAGGGCCGGG  ATTGAGGCGG  GTCAAGGCCG  GTAAGAGGCG  GGGTACCGAC  TGATTAAAAA  AAATAAATAC sty I                                        scrFI
                                                                        avr II                                       nci I
              fnu4HI                                                    hae III                                      msp I
              bgl I                                                     stu I                                        hpa II
              sfi I          dde I                                      hae I                                        hae III
     hae III  hae III        mnl I   alu I                              mnl I                                        xmaI
     mnl I    mnl I  hae III mnl I                                                                                   eagI
                                                                                                                     eaeI
                                                                                                                     cfrI
301  CAGAGGCCGA  GGCCGCCTCG  GCCTCTGAGC  TATTCCAGAA  GTAGTGAGGA  GGCTTTTTTG  GAGGCCTAGG  CTTTTGCAAA  AAGCTTATCC  GGCCGGGAAC
     GTCTCCGGCT  CCGGCGGAGC  CGGAGACTCG  ATAAGGTCTT  CATCACTCCT  CCGAAAAAAC  CTCCGGATCC  GAAAACGTTT  TTCGAATAGG  CCGGCCCTTG bstXI
                                                                sau96I
                                                                hae III                                            fnu4HI
                       hinf I                                   asu I                                              tha I
              tha I               ple I                                                                            fnu DII
              fnuDII              hinf I                                                                           bstUI     ase I
              bstUI  rsa I                                              sty I                         sp6 promoter
401  GGTGCATTGG  AACGCGGATT  CCCCGTGCCA  AGAGTCAGGT  AAGTACCGCC  TATAGAGTCT  ATAGGCCCAC  CCCCTTGGCT  TCGTTAGAAC  GCGGCTACAA
     CCACGTAACC  TTGCGCCTAA  GGGGCACGGT  TCTCAGTCCA  TTCATGCGGG  ATATCTCAGA  TATCCGGGTG  GGGGAACCGA  AGCAATCTTG  CGCCGATGTT
                                U1 matched splice donar
```

Fig.10(cont.)

```
           sau3AI
           mboI
           dpnI
           alwI
           xhoII
           nlaIV
           bstYI
           bamHI                                                                                    sau96I
           alwI            fokI                                                                     avaII
         removed ATG                                                                                asuI              thaI aluI
                U2 match                                                                            scrFI             fnuDII
                         lariat consensus                                                           ecoRII            bstUI
                         IgG vH natural lariat restored                                             bstNI     mnlI    nruI hindIII
                                                                                                       cloning linker
 mseI
501 TTAATACATA ACCTTTTGGA TCCTACTGAC ACTGACATCC ACTTTTTCTT TTTCTCCACA GGTGTCCACT CCCAGGTCCA ACTGCACCTC GGTTCGCGAA
    AATTATGTAT TGGAAAACCT AGGATGACTG TGACTGTAGG TGAAAAAGAA AAAGAGGTGT CCACAGGTGA GGGTCCAGGT TGACGTGGAG CCAAGCGCTT
         bspMI
       pstI
      fnu4HI
       bbvI            mseI      hgaI
    1
601 GCTTGGGCTG CAGGTCGCCG TGAATTTAAG GGACGCTGTG AAGCA
    CGAACCCGAC GTCCAGCGGC ACTTAAATTC CCTGCGACAC TTCGT
```

HUMAN DNASE

This is a continuation application claiming priority to application Ser. No. 10/005,675, filed Nov. 7, 2001, now abandoned, which is a continuation of application Ser. No. 09/669,306, filed Sep. 25, 2000, now abandoned, which is a continuation of application Ser. No. 08/761,578, filed Dec. 9, 1996, now abandoned, which is a continuation application of application Ser. No. 08/528,876, filed Sep. 15, 1995. now abandoned, which is a continuation of application Ser. No. 08/117,584, filed Sep. 3, 1993, now abandoned, which is a divisional of application Ser. No. 07/914,226, filed 13 Jul. 1992, now abandoned, which is a continuation of application Ser. No. 07/448,038, filed Dec. 8, 1989, now abandoned, which is a continuation-in-part of application Ser. No. 07/289,958, filed Dec. 23, 1988, now abandoned, to which applications priority is claimed under 35 USC §120, the entire disclosures of which are hereby incorporated by reference.

DNase is a phosphodiesterase capable of hydrolyzing polydeoxyribonucleic acid. It acts to extensively and non-specifically degrade DNA and in this regard is distinguished from the relatively limited and sequence-specific restriction endonucleases. This invention is concerned principally with DNase I and II. DNase I has a pH optimum near neutrality, an obligatory requirement for divalent cations, and produces 5'-phosphate nucleotides on hydrolysis of DNA. DNase II exhibits an acid pH optimum, can be activated by divalent cations and produces 3'-phosphate nucleotides on hydrolysis of DNA. Multiple molecular forms of DNase I and II also are known.

DNase from various species has been purified to varying degree. Bovine DNase A, B, C, and D was purified and completely sequenced as early as 1973 (Liao et al., J. Biol. Chem. 248:1489 [1973]; Salnikow et al., J. Biol. Chem. 248:1499 [1973]; Liao et al., J. Biol. Chem. 249:2354 [1973]). Porcine and ovine DNase have been purified and fully sequenced (Paudel et al., J. Biol. Chem. 261:16006 [1986] and Paudel et al., J. Biol. Chem. 261:16012 [1986]). Human urinary DNase was reported to have been purified to electrophoretically homogeneous state and the N-terminal amino acid observed to be leucine; no other sequence was reported (Ito et al., J. Biochem. 95:1399 [1984]; see also Funakoshi et al., J. Biochem. 82:1771 [1977]; Murai et al., Biochim. et Biophys. Acta 517:186 [1978] and Wroblewski et al., P.S.E.B.M. 74:443 [1950]).

Notwithstanding that full sequence information for a mammalian DNase first became known in 1973, only recently has a report appeared of an attempt to clone and express this class of enzymes. Shields et al. describe the expression cloning of part of the gene for bovine DNase I and expression of a fusion product in E. coli which was biologically and immunologically active (Biochem. Soc. Trans. 16:195 [1988]). The DNase product of Shields et al., however, was toxic to the host cells and could only be obtained by the use of an inducible promoter. Furthermore, great difficulty was encountered in attempts to isolate plasmid DNA from either clone, an obstacle attributed to constitutive levels of expression of DNase from the clones, so that these authors were unable to determine the sequence for the DNase-encoding nucleic acid. According to Shields et al., the inability to recover the plasmid was the result of constitutive expression of DNase even when the promoter was repressed at low temperature. This would create a considerable obstacle since Shields et al. had only identified the clone by expression cloning, which necessarily requires that the DNase be placed under the control of a promoter of some sort.

DNase finds a number of known utilities, and has been used for therapeutic purposes. Its principal therapeutic use has been to reduce the viscosity of pulmonary secretions in such diseases as pneumonia, thereby aiding in the clearing of respiratory airways. Obstruction of airways by secretions can cause respiratory distress, and in some cases, can lead to respiratory failure and death. Bovine pancreatic DNase has been sold under the tradename Dornavac (Merck), but this product was withdrawn from the market. Reports indicate that this product had some clinical efficacy. However, although some clinicians observed no significant side effects (Lieberman, JAMA 205:312 [1968]), others noted serious complications such as pulmonary irritation and anaphylaxis (Raskin, Am. Rev. Resp. Dis., 98:697 [1968]). Such complications may be attributed to the fact that the previously marketed products were contaminated with proteases and were immunogenic in humans. In fact, although the clinical problem of thick pulmonary secretions is often chronic and recurring, prolonged therapy with bovine pancreatic DNase was not recommended. These problems could be overcome by providing DNase of human origin and producing it in large quantities in nonpancreatic exocrine cells to facilitate purification free of contaminant proteases.

Accordingly, it is an object of this invention to provide nucleic acid encoding human DNase.

It is another object to provide a method for expression of human DNase in recombinant cell culture.

A further object is to enable the preparation of DNase having variant amino acid sequences or glycosylation not otherwise found in nature, as well as other derivatives of DNase, having improved properties including enhanced specific activity.

SUMMARY OF THE INVENTION

The objects of this invention have been accomplished by a method comprising providing nucleic acid encoding human DNase; transforming a host cell with the nucleic acid; culturing the host cell to allow DNase to accumulate in the culture; and recovering DNase from the culture. Surprisingly, a full length clone encoding human DNase has been identified and recovered, and moreover this DNA is readily expressed by recombinant host cells.

In preferred embodiments the mammalian DNase is full-length, mature human DNase, having the amino acid sequence of native human DNase, its naturally occurring alleles, or predetermined amino acid sequence or glycosylation variants thereof. The nucleic acid encoding the DNase preferably encodes a preprotein which is processed and secreted from host cells, particularly mammalian cells.

BRIEF DESCRIPTION OF THE FIGURES

FIG. 1 depicts the amino acid and DNA sequence of human DNase. The native signal sequence is underlined, the potential initiation codons are circled, and the mature sequence is bracketed.

FIG. 2 shows a comparison between the amino acid sequence for mature human (hDNase) and bovine (bDNase) DNase. Asterisks denominate exact homology, periods designate conserved substitutions.

FIG. 6 shows the complete nucleotide sequence of pSVI.DNase up to, but not including, the coding region of DNase.

FIG. 7 shows the complete nucleotide sequence of pSVI2.DNase up to, but not including, the coding region of DNase.

FIG. 8 shows the complete nucleotide sequence of pSVI3.DNase up to, but not including, the coding region of DNase.

FIG. 9 shows the complete nucleotide sequence of pSVI5.DNase up to, but not including, the coding region of DNase.

FIG. 10 shows the complete nucleotide sequence of pSVI6B.DNase up to, but not including, the coding region of DNase.

DETAILED DESCRIPTION

Figure 1:
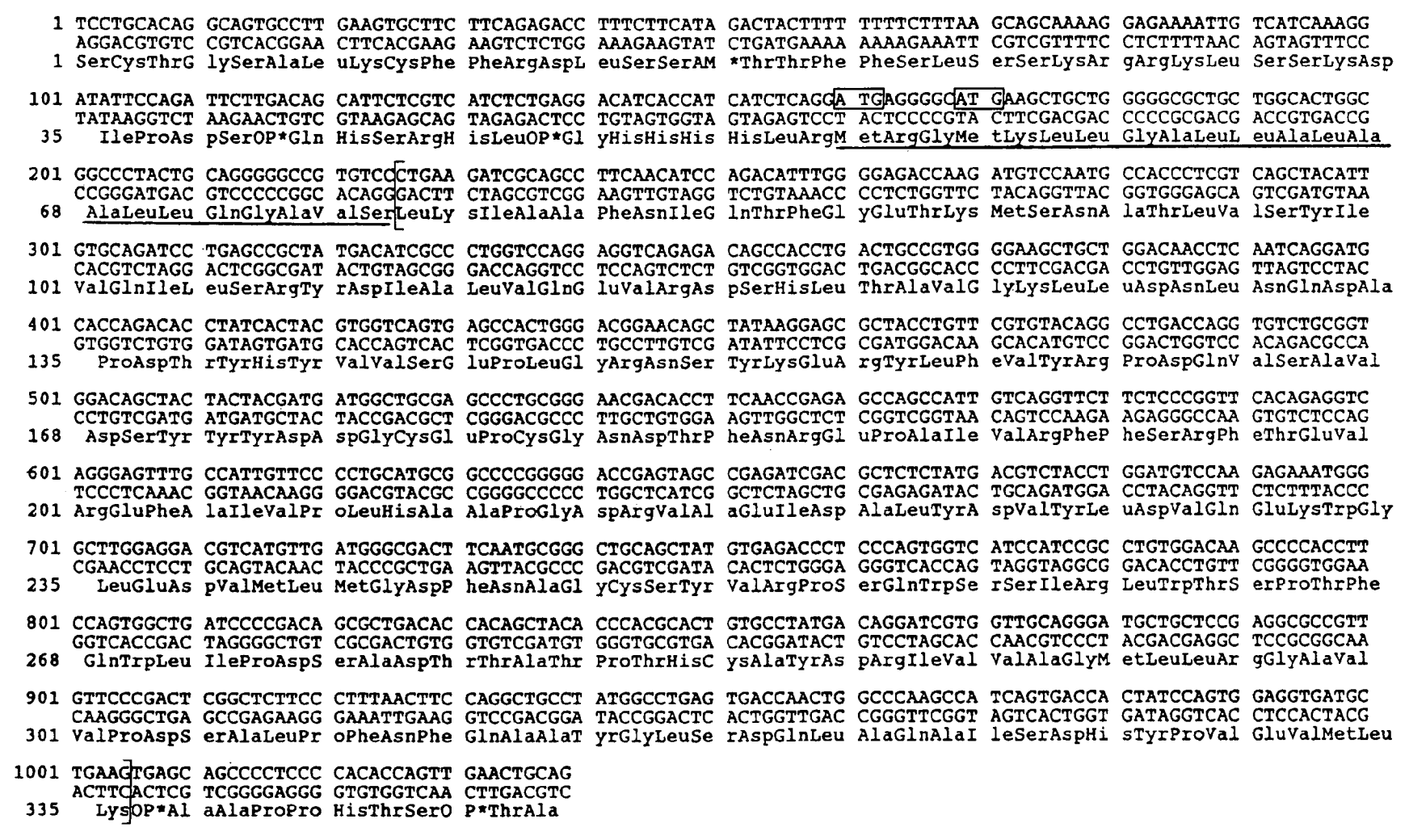
Figure 3:
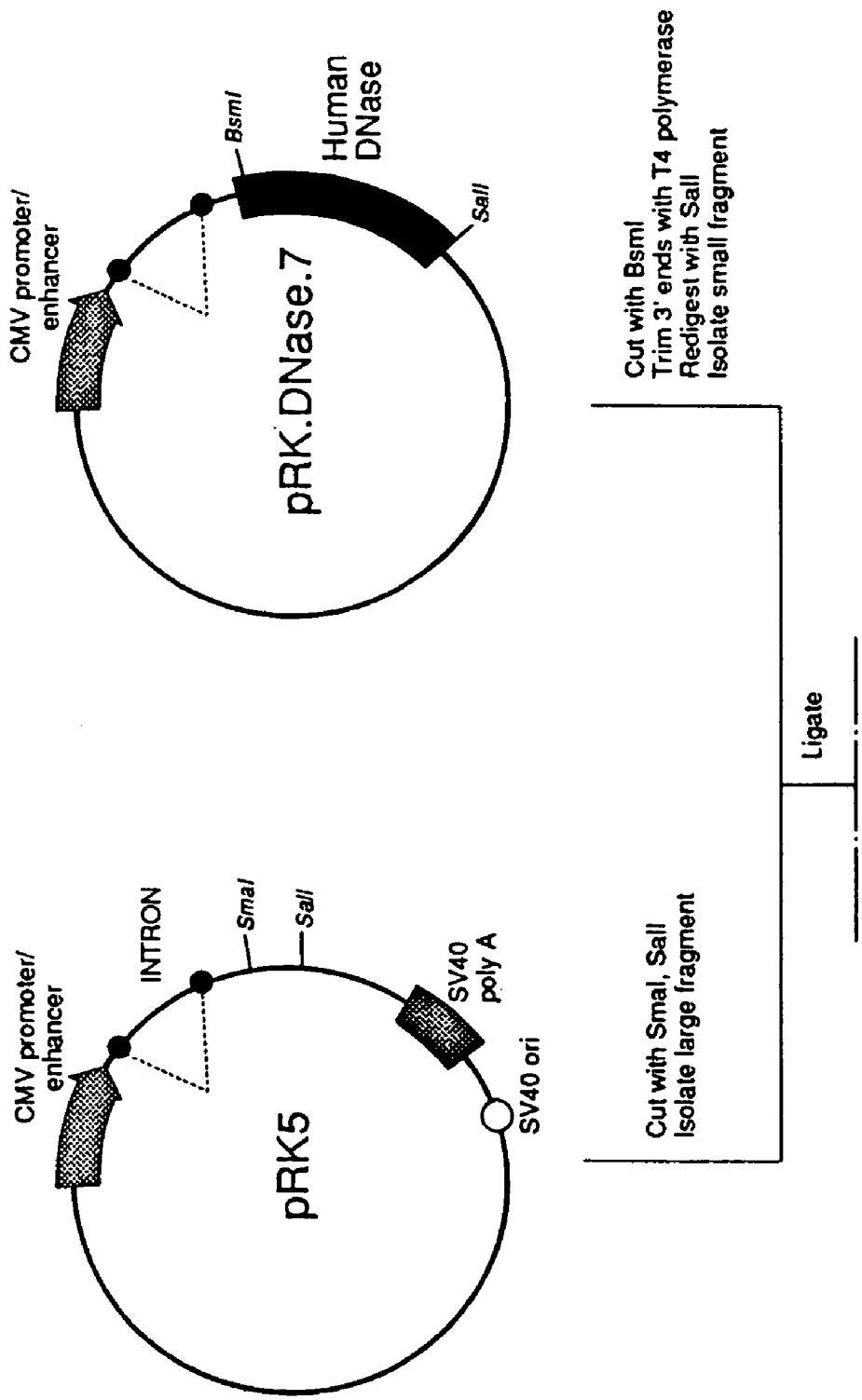
FIG. 3 shows the construction of the expression vectors pRK.DNase.3 and pSVe.DNase.

Human DNase is defined as a polypeptide having the amino acid sequence of FIG. 1 together with amino acid sequence variants thereof which retain the qualitative enzymatic activity of DNase. Preferably, the variants are not immunogenic in humans. Variants may possess greater enzymatic activity, enhanced resistance to inhibition (in particular by actin), improved solubility, or may be expressed at higher levels by host cells.

Amino acid sequence variants of DNase fall pinto one or more of three classes: Substitutional, insertional or deletional variants. These variants ordinarily are prepared by site specific mutagenesis of nucleotides in the DNA encoding the DNase, by which DNA encoding the variant is obtained, and thereafter expressing the DNA in recombinant cell culture. However, variant DNase fragments having up to about 100-150 residues may be prepared conveniently by in vitro synthesis.

The amino acid sequence variants of human DNase are predetermined or are naturally occurring alleles. For example, bovine pancreatic DNase is found naturally as 4 molecular variants which possess the same enzymatic activity but differ in glycosylation pattern or substitution at the amino acid level. Additionally, human DNase is found naturally with an arginine or a glutamine residue at amino acid 222. The variants typically exhibit the same qualitative biological activity as the naturally-occurring analogue. Specifically excluded from the scope of human DNase as described herein are the sequences of naturally occurring bovine, porcine or ovine DNase.

While the site for introducing an amino acid sequence variation is predetermined, the mutation per se need not be predetermined. For example, in order to optimize the performance of a mutation at a given site, saturation mutagenesis is introduced at the target codon or region and the DNase variants then screened for the optimal combination of desired activity.

Amino acid substitutions are typically introduced for single residues; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. Obviously, the mutations that will be made in the DNA encoding the variant DNase must not place the sequence out of reading frame and preferably will not create complementary regions that could produce secondary MRNA structure (EP 75,444A).

Substitutional variants are those in which at least one residue in the FIG. 1 sequence has been removed and a different residue inserted in its place. Such substitutions generally are made in accordance with the following Table 1 when it is desired to finely modulate the characteristics of DNase.

TABLE 1

| Original Residue | Exemplary Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in DNase properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Examples of human DNase amino acid sequence variants are described in the table below. The residue following the residue number indicates the replacement or inserted amino acids.

TABLE 2

| Substitutions | |
|---|---|
| H134K, N, R or Q | FGW, L, I, M or V |
| A135S | 18F, L, V, M or W |
| L133V, I or A | R41K or H |
| P132A | S43T, C or Y |
| N18K, H, R or Q | K77R or H |
| S17T | R79K or H |
| T20S or Y | N110D, S, T, R, Y or Q |
| N106K, H, R or Q | G167P |
| G105P or A | F169L, V, I or M |
| D107E or T | A171G, V or M |
| R140A | S250T, Y or M |
| R121K or H | Y253T, S or M |
| T108S or Y | R73N |
| P103S, T or Y | R73C + D139C |
| C101S, T, Y or M | K260R or S |
| C104S, T, Y or H | L259V, I or M |

| Deletions | Insertions |
|---|---|
| Δ34H-Δ39E | K260RA-COOH |
| Δ159G-161E | V131A P132 |
| Δ204A-208H | P132A L133 |
| Δ121R-127E | |
| Δ188T-191T | |
| Δ204A-208H | |
| Δ223G-231L | |
| Δ260K | |

In general, sequence variation is introduced into residues 6-10, 41-43, 77-79, 110-112, 167-171, 250-253, 73, 93, 157, 149, 185, 187, 198, 17-20, 105-108 and 131-139. Preferably, the variants represent conservative substitutions. It will be understood that some variants may exhibit reduced or absent hydrolytic activity. These variants nonetheless are useful as standards in immunoassays for DNase so long as they retain at least one immune epitope of native human DNase.

Glycosylation variants are included within the scope of human DNase. Included are unglycosylated amino acid sequence variants, unglycosylated DNase having the native, unmodified amino acid sequence of DNase, and glycosylation variants. For example, substitutional or deletional mutagenesis is employed to eliminate the N-linked glycosylation sites of human DNase found at residues 18 and 106, e.g., the asparagine residue is deleted or substituted for by another basic residue such as lysine or histidine. Alternatively, flanking residues making up the glycosylation site are substituted for or deleted, even though the asparagine residues remain unchanged, in order to prevent glycosylation by eliminating the glycosylation recognition site. Unglycosylated DNase which has the amino acid sequence of native human DNase is produced in recombinant prokaryotic cell culture because prokaryotes are incapable of introducing glycosylation into polypeptides. In addition, glycosylation variants may be generated by adding potential N-linked glycosylation sites through inserting (either by amino acid substitution or deletion) consensus sequences for N-linked glycosylation: Asn-X-Ser or Asn-X-Thr. Glycosylation variants may be generated by both eliminating the N-linked glycosylation sites at residues 18 and 106 and by adding new ones.

Glycosylation variants, i.e., glycosylation which is different from that of human pancreatic or urinary DNase, are produced by selecting appropriate host cells or by In vitro methods. Yeast, for example, introduce glycosylation which varies significantly from that of mammalian systems. Similarly, mammalian cells having a different species (e.g. hamster, murine, insect, porcine, bovine or ovine) or tissue origin (e.g. lung, liver, lymphoid, mesenchymal or epidermal) than the source of the DNase are screened for the ability to introduce variant glycosylation as characterized for example by elevated levels of mannose or variant ratios of mannose, fucose, sialic acid, and other sugars typically found in mammalian glycoproteins. In addition, mammalian or yeast cells which possess mutations with respect to glycosylation phenotype may be identified, selected for following mutation, or constructed and utilized to produce DNase. In vitro processing of DNase typically is accomplished by enzymatic hydrolysis, e.g. neuraminidase or endoglycosydase H digestion.

Insertional amino acid sequence variants of DNases are those in which one or more amino acid residues are introduced into a predetermined site in the target DNase and which displace the preexisting residues. Most commonly, insertional variants are fusions of heterologous proteins or polypeptides to the amino or carboxyl terminus of DNase. DNase derivatives which are immunogenic in humans are not preferred, e.g. those which are made by fusing an immunogenic polypeptide to DNase by cross-linking in vitro or by recombinant cell culture transformed with DNA encoding immunogenic fusions such as lacZ. For this reason, the typical insertional variants contemplated herein are the signal sequence variants described above.

Covalent modifications of the DNase molecule are included within the scope hereof. Such modifications are introduced by reacting targeted amino acid residues of the recovered protein with an organic derivatizing agent that is capable of reacting with selected side chains or terminal residues, or by harnessing mechanisms of post-translational modification that function in selected recombinant host cells. The resulting covalent derivatives are useful in programs directed at identifying residues important for biological activity, for immunoassays of DNase or for the preparation of anti-human DNase antibodies for immunoaffinity purification of recombinant DNase. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue.

Cysteinyl residues most commonly are reacted with α-haloacetates (and corresponding amines), such as chloracetic acid or chloroacetamide to give carboxymethyl or carboxamidomethyl derivatives. Cysteinyl residues also are derivatized by reaction with bromotrifluoroacetone, α-bromo-β-(5-imidozoyl) propionic acid, chloroacetol phosphate, N-alkylmaleimides, 3-nitro-2-pyridyl disulfide, methyl 2-pyridyl disulfide, p-chloromercuribenzoate, 2-chloromercuri-4-nitrophenol or chloro-7-nitrobenzo-2-oxa-1,3-diazole.

Histidyl residues preferably are derivatized by reaction with diethylpyrocarbonate at pH 5.5 to 7.0 because this agent is relatively specific for the histidyl side chain. Para-bromo-phenacyl bromide also is useful; the reaction should be performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a amino-containing residues include imidoesters such as methyl picolinimidate; pyridoxal phosphate; pyridoxal; cloroborohydride; trinitrobenzenesulfonic acid; O-methylisourea; 2,4-pentanedione; and transaminase-catalyzed reaction with glyoxylate.

Arginyl residues are modified by reaction with one of several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine ϵ-amino group.

The specific modification of tyirsyl residues per se has been extensively studied, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labelled proteins for use in radioimmunoassay, the chloramine T method being widely adopted per se for this purpose.

Carboxyl side groups (aspartyl or glutamyl) are selectively modified by reaction with carbodiimides (R'—N=C=N—R') such as 1-cyclohexyl-3-(2-morpholinyl-(4)-ethyl) carbodiimide or 1-ethyl-3-(4-azonia-4,4-dimethylpentyl)-carbodiimide. Furthermore, aspartyl and glutamyl residues are converted to asparaginyl and glutaminyl residues by reaction with ammonium ions, this being an alternative to mutating the nucleic acid to encode asparagine are glutamine.

Derivatization with bifunctional agents is useful for preparing intermolecular aggregates of the protein with immunogenic polypeptides as well as for cross-linking the protein to a water insoluble support matrix or surface for use in the assay or affinity purification of antibody. In addition, a study of intrachain cross-links will provide direct information on conformational structure. Commonly used cross-linking agents include 1,1-bis(diazoacetyl)-2-phenylethane, glutaraldehyde, N-hydroxysuccinimide esters, for example esters with 4-azidosalicylic acid, homobifunctional imidoesters including disuccinimidyl esters such as 3,3'-dithiobis (succinimidyl-propionate), and bifunctional maleimides such as bis-N-maleimido-1,8-octane. Derivatizing agents such as methyl-3-[(p-azido-phenyl)dithio] propioimidate yield photoactivatable intermediates which are capable of forming cross-links in the presence of light. Alternatively, reactive water insoluble matrices such as cyanogen bromide activated carbohydrates and the reactive substrates described in U.S. Pat. Nos. 3,969,287; 3,691,016; 4,195,128; 4,247,642; 4,229,537 and 4,330,440 are employed for protein immobilization.

Certain post-translational derivatizations are the result of the action of recombinant host cells on the expressed polypeptide. Glutaminyl and asparaginyl residues are frequently post-translationally-deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl or threonyl residues, methylation of the α-amino groups of lysine, arginine, and hystidine side chains (T. E. Creighton, *Proteins: Structure and Molecular Properties*, W.H. Freeman & Co., San Francisco pp 79-86 [1983]), acetylation of the N-terminal amine and, in some instances, amidation of the C-terminal carboxyl.

Other derivatives comprise the polypeptide of this invention covalently bonded to a nonproteinaceous polymer. The nonproteinaceous polymer ordinarily is a hydrophilic synthetic polymer, i.e., a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyalkylene ethers such as polyethylene glycol, polypropylene glycol, polyoxyetbylene esters or methoxy polyethylene glycol; polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopoly-saccharides, e.g. hyaluronic acid; polymers of sugar alcohols such as polysorbitol and polymannitol; and heparin or heparon. Where the polysaccharide is the native glycosylation or the glycosylation attendant on recombinant expression, the site of substitution may be located at other than a native N or O-linked glycosylation site wherein an additional or substitute N or O-linked site has been introduced into the molecule. Mixtures of such polymers are employed, or the polymer may be homogeneous. The polymer prior to crosslinking need not be, but preferably is, water soluble, but the final conjugate must be water soluble. In addition, the polymer should not be highly immunogenic in the conjugate form, nor should it possess viscosity that is incompatible with intravenous infusion or injection if it is intended to be administered by such routes.

Preferably the polymer contains only a single group which is reactive. This helps to avoid cross-linking of protein molecules. However, it is within the scope herein to optimize reaction conditions to reduce cross-linking, or to purify the reaction products through gel filtration or chromatographic sieves to recover substantially homogeneous derivatives.

The molecular weight of the polymer ranges about from 100 to 500,000, and preferably is about from 1,000 to 20,000. The molecular weight chosen will depend upon the nature of the polymer and the degree of substitution. In general, the greater the hydrophilicity of the polymer and the greater the degree of substitution, the lower the molecular weight that can be employed. Optimal molecular weights will be determined by routine experimentation.

The polymer generally is covalently linked to the polypeptide herein through a multifunctional crosslinking agent which reacts with the polymer and one or more amino acid or sugar residues of the protein. However, it is within the scope of this invention to directly crosslink the polymer by reacting a derivatized polymer with the protein, or vice versa.

The covalent crosslinking site on the polypeptide includes the N-terminal amino group and epsilon amino groups found on lysine residues, as well as other amino, imino, carboxyl, sulfhydryl, hydroxyl or other hydrophilic groups. The polymer may be covalently bonded directly to the protein without the use of a multifunctional (ordinarily bifunctional) crosslinking agent. Examples of such crosslinking agents include 1,1-bis(diazoacetyl)-2-phenylethane, glutaraldehyde, N-hydroxysuccinimide esters, for example esters with 4-azidosalicylic acid, homobifunctional imidoesters including disuccinimidyl esters such as 3,3'-dithiobis (succinimidyl-propionate), and bifunctional maleimides such as bis-N-maleimido-1,8-octane. Derivatizing agents such as methyl-3-[(p-azido-phenyl)dithio] propioimidate yield photoactivatable intermediates which are capable of forming cross-links in the presence of light. Alternatively, reactive water soluble-matrices such as cyanogen bromide activated carbohydrates and the systems described in U.S. Pat. Nos. 3,959,080; 3,969,287; 3,691,016; 4,195,128; 4,247,642; 4,229,537; 4,055,635 and 4,330,440 are suitably modified for cross-linking. Covalent bonding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, succinimidyl active esters, activated dithiocarbonate PEG, 2,4,5-trichlorophenylchloroformate or p-nitrophenylchloroformate activated PEG. Carboxyl groups are derivatized by coupling PEG-amine using carbodiimide.

Polymers are conjugated to oligosaccharide groups by oxidation using chemicals, e.g. metaperiodate, or enzymes, e.g. glucose or galactose oxidase, (either of which produces the aldehyde derivative of the carbohydrate), followed by reaction with hydrazide or amino-derivatized polymers, in the same fashion as is described by Heitzmann et al., P.N.A.S., 71:3537-3541 (1974) or Bayer et al., Methods in Enzymology, 62:310 (1979), for the labeling of oligosaccharides with biotin or avidin. Further, other chemical or enzymatic methods which have been used heretofore to link oligosaccharides and polymers may be suitable. Substituted oligosaccharides are particularly advantageous because, in general, there are fewer substitutions than amino acid sites for derivatization, and the oligosaccharide products thus will be more homogeneous. The oligosaccharide substituents also are optionally modified by enzyme digestion to remove sugars, e.g. by neuraminidase digestion, prior to polymer derivatization.

The polymer will bear a group which is directly reactive with an amino acid side chain, or the N— or C— terminus of the polypeptide herein, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides.

"Water soluble" in reference to the polymer conjugate means that the conjugate is soluble in physiological fluids such as blood in an amount which is sufficient to achieve a therapeutically effective concentration.

"Water soluble" in reference to the starting polymer means that the polymer or its reactive intermediate used for conjugation is sufficiently water soluble to participate in a derivatization reaction.

The degree of substitution with polymer will vary depending upon the number of reactive sites on the protein, whether all or a fragment of protein is used, whether the protein is a fusion with a heterologous protein, the molecular weight, hydrophilicity and other characteristics of the polymer, and the particular protein derivatization sites chosen. In general, the conjugate contains about from 1 to 10 polymer molecules, while any heterologous sequence may be substituted with an essentially unlimited number of polymer molecules so long as the desired activity is not significantly adversely affected. The optimal degree of crosslinking is easily determined by an experimental matrix in which the time, temperature and other reaction conditions are varied to change the degree of substitution, after which the ability of the conjugates to function in the desired fashion is determined.

The polymer, e.g. PEG, is crosslinked by a wide variety of methods known per se for the covalent modification of proteins with nonproteinaceous polymers such as PEG. Certain of these methods, however, are not preferred for the purposes herein. Cyanuric chloride chemistry leads to many side reactions, including protein cross-linking. In addition, it may be particularly likely to lead to inactivation of proteins containing sulfhydryl groups. Carbonyl diimidazole chemistry (Beauchamp et al., "Anal. Biochem." 131:25-33 [1983]) requires high pH (>8.5), which can inactivate proteins. Moreover, since the "activated PEG" intermediate can react with water, a very large molar excess of "activated PEG" over protein is required. The high concentrations of PEG required for the carbonyl diimidazole chemistry also led to problems with purification, as both gel filtration chromatography and hydrophobic interaction chromatography are adversely effected. In addition, the high concentrations of "activated PEG" may precipitate protein, a problem that per se has been noted previously (Davis, U.S. Pat. No. 4,179,337). On the other hand, aldehyde chemistry (Royer, U.S. Pat. No. 4,002,531) is more efficient since it requires only a 40 fold molar excess of PEG and a 1-2 hr incubation. However, the manganese dioxide suggested by Royer for preparation of the PEG aldehyde is problematic "because of the pronounced tendency of PEG to form complexes with metal-based oxidizing agents" (Harris et al., "J. Polym. Sci., Polym. Chem. Ed." 22:341-352 [1984]). The use of a moffatt oxidation, utilizing DMSO and acetic anhydride, obviates this problem. In addition, the sodium borohydride suggested by Royer must be used at a high pH and has a significant tendency to reduce disulfide bonds. In contrast, sodium cyanoborohydride, which is effective at neutral pH and has very little tendency to reduce disulfide bonds is preferred.

The conjugates of this invention are separated from unreacted starting materials by gel filtration. Heterologous species of the conjugates are purified from one another in the same fashion.

The polymer also may be water insoluble, as a hydrophilic gel or a shaped article. Particularly useful are polymers comprised by surgical tubing such as catheters or drainage conduits.

DNA encoding human DNase is synthesized by in vitro methods or is obtained readily from human pancreatic cDNA libraries. Since FIG. 1 gives the entire DNA sequence for human DNase, one needs only to conduct hybridization screening with labelled DNA encoding human DNase or fragments thereof (usually, greater than about 50 bp) in order to detect clones in the cDNA libraries which contain homologous sequences, followed by analyzing the clones by restriction enzyme analysis and nucleic acid sequencing to identify full-length clones. If full length clones are not present in the library, then appropriate fragments may be recovered from the various clones and ligated at restriction sites common to the fragments to assemble a full-length clone. DNA encoding DNase from other animal species is obtained by probing libraries from such species with the human sequence, or by synthesizing the genes in vitro (for bovine, porcine or ovine DNase).

Included within the scope hereof are nucleic acid probes which are capable of hybridizing under high stringency conditions to the cDNA of human DNase or to the genomic gene for human DNase (including introns and 5' or 3' flanking regions extending to the adjacent genes or about 5,000 bp, whichever is greater). Identification of the genomic DNA for DNase is a straight-forward matter of probing a human genomic library with the cDNA or its fragments which have been labelled with a detectable group, e.g. radiophosphorus, and recovering clone(s) containing the gene. The complete gene is pieced together by "walking" if necessary. Typically, the probes do not encode bovine, ovine or porcine DNase, and they range about from 10 to 100 bp in length.

In general, prokaryotes are used for cloning of DNA sequences in constructing the vectors useful in the invention. For example, E. coli K12 strain 294 (ATCC No. 31446) is particularly useful. Other microbial strains which may be used include E. coli B and E. coli X1776 (ATCC No. 31537). These examples are illustrative rather than limiting. Alternatively, in vitro methods of cloning, e.g., PCR, are suitable.

DNase is expressed directly in recombinant cell culture as an N-terminal methionyl analogue, or as a fusion with a polypeptide heterologous to human DNase, preferably a signal sequence or other polypeptide having a specific cleavage site at the N-terminus of the DNase. For example, in constructing a prokaryotic secretory expression vector the native DNase signal is employed with hosts that recognize the human signal. When the secretory leader is "recognized" by the host, the host signal peptidase is capable of cleaving a fusion of the leader polypeptide fused at its C-terminus to the desired mature DNase. For host prokaryotes that do not process the human signal, the signal is substituted by a prokaryotic signal selected for example from the group of the alkaline phosphatase, penicillinase, lpp or heat stable enterotoxin II leaders. For yeast secretion the human DNase signal may be substituted by the yeast invertase, alpha factor or acid phosphatase leaders. In mammalian cell expression the native signal is satisfactory, although other mammalian secretory protein signals are suitable, as are viral secretory leaders, for example the herpes simplex gD signal.

DNase is expressed in any host cell, but preferably is synthesized in mammalian hosts. However, host cells from prokaryotes, fungi, yeast, pichia, insects and the like are also are used for expression. Exemplary prokaryotes are the strains suitable for cloning as well as E. coli W3110 (F⁻, λ⁻ prototrophic, ATTC No. 27325), other enterobacteriaceae such as *Serratia marcescans*, bacilli and various pseudomonads. Preferably the host cell should secrete minimal amounts of proteolytic enzymes.

Expression hosts typically are transformed with DNA encoding human DNase which has been ligated into an expression vector. Such vectors ordinarily carry a replication site (although this is not necessary where chromosomal integration will occur). It is presently preferred to utilize an expression vector as described in Example 4 below, where the vector contains a splice-donor-intron-splice-acceptor sequence or unit.

Expression vectors also include marker sequences which are capable of providing phenotypic selection in transformed cells. For example, E. coli is typically transformed using pBR322, a plasmid derived from an E. coli species (Bolivar, et al., Gene 2: 95 [1977]). pBR322 contains genes for ampicillin and tetracycline resistance and thus provides easy means for identifying transformed cells, whether for purposes of cloning or expression. Expression vectors also optimally will contain sequences which are useful for the control of transcription and translation, e.g., promoters and Shine-Dalgarno sequences (for prokaryotes) or promoters and enhancers (for mammalian cells). The promoters may be, but need not be, inducible; surprisingly, even powerful constitutive promoters such as the CMV promoter for mammalian hosts have been found to produce DNase without host cell toxicity. While it is conceivable that expression vectors need not contain any expression control, replicative sequences or selection genes, their absence may hamper the identification of DNase transformants and the achievement of high level DNase expression.

Promoters suitable for use with prokaryotic hosts illustratively include the β-lactamase and lactose promoter systems (Chang et al., "Nature", 275: 615 [1978]; and Goeddel et al., "Nature" 281: 544 [1979]), alkaline phosphatase, the tryptophan (trp) promoter system (Goeddel "Nucleic Acids Res." 8: 4057 [1980] and EPO Appln. Publ. No. 36,776) and hybrid promoters such as the tac promoter (H. de Boer et al., "Proc. Natl. Acad. Sci. USA" 80: 21-25 [1983]). However, other functional bacterial promoters are suitable. Their nucleotide sequences are generally known, thereby enabling a skilled worker operably to ligate them to DNA encoding DNase (Siebenlist et al., "Cell" 20: 269 [1980]) using linkers or adaptors to supply any required restriction sites. Promoters for use in bacterial systems also will contain a Shine-Dalgarno (S.D.) sequence operably linked to the DNA encoding DNase.

In addition to prokaryotes, eukaryotic microbes such as yeast, or filamentous fungi are satisfactory. *Saccharomyces cerevisiae* is the most commonly used eukaryotic microorganism, although a number of other strains are commonly available. Strains of *Saccharomyces cerevisiae* having the identifying characteristics of strain AB107-30(4)-VN#2 (ATCC Accession No. 20937), particularly its resistance to 4M orthovanadate, is particularly suitable for DNase expression (see U.S. Ser. No. 07/343,863, filed 26 Apr. 1989, specifically incorporated by reference). With this VN#2 strain, it is desirable to stably transform the cells with a high-copy-number plasmid derived-from a yeast 2-micron plasmid, id. Generally, the plasmid YRp7 is a satisfactory expression vector in yeast (Stinchcomb, et al., Nature 282: 39 [1979]; Kingsman et al., Gene 7: 141 [1979]; Tschemper et al., Gene 10: 157 [1980]). This plasmid already contains the trpl gene which provides a selection marker for a mutant strain of yeast lacking the ability to grow in tryptophan, for example ATCC no. 44076 or PEP4-1 (Jones, Genetics 85: 12 [1977]). The presence of the trpl lesion as a characteristic of the yeast host cell genome then provides an effective environment for detecting transformation by growth in the absence of tryptophan. Expression in pichia (U.S. Pat. No. 4,808,537) is also satisfactory.

Suitable promoting sequences for use with yeast hosts include the promoters for 3-phosphoglycerate kinase (Hitzeman et al., "J. Biol. Chem." 255: 2073 [1980]) or other glycolytic enzymes (Hess et al., "J. Adv. Enzyme Reg." 7: 149 [1968]; and Holland, "Biochemistry" 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., European Patent Publication No. 73,657A.

Expression control sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence which may be the signal for addition of the poly A tail to the 3' end of the coding sequence. All of these sequences may be inserted into mammalian expression vectors.

Suitable promoters for controlling transcription from vectors in mammalian host cells are readily obtained from various sources, for example, the genomes of viruses such as polyoma virus, SV40, adenovirus, MMV (steroid inducible), retroviruses (e.g. the LTR of HIV), hepatitis-B virus and most preferably cytomegalovirus, or from heterologous mammalian promoters, e.g. the beta actin promoter. The early and late promoters of SV40 are conveniently obtained as an SV40 restriction fragment which also contains the SV40 viral origin of replication. Fiers et al., Nature, 273: 113 (1978). The immediate early promoter of the human cytomegalovirus is conveniently obtained as a HindIII E restriction fragment. Greenaway, P. J. et al., Gene 18: 355-360 (1982).

Transcription of a DNA encoding DNase by higher eukaryotes is increased by inserting an enhancer sequence into the vector. Enhancers are cis-acting elements of DNA, usually about from 10-300 bp, that act on a promoter to increase its transcription. Enhancers are relatively orientation and position independent having been found 5' (Laimins, L. et al., PNAS 78: 993 [1981]) and 3' (Lusky, M. L., et al., Mol. Cell Bio. 3: 1108 [1983]) to the transcription unit, within an intron (Banerji, J. L. et al., Cell 33: 729 [1983]) as well as within the coding sequence itself (Osborne, T. F., et al., Mol. Cell Bio. 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the MRNA encoding DNase. The 3' untranslated regions also include transcription termination sites.

Expression vectors may contain a selection gene, also termed a selectable marker. Examples of suitable selectable markers for mammalian cells are dihydrofolate reductase (DHFR), thymidine kinase (TK) or neomycin. When such selectable markers are successfully transferred into a mammalian host cell, the transformed mammalian host cell is able to survive if placed under selective pressure. There are two widely used distinct categories of selective regimes. The first category is based on a cell's metabolism and the use of a mutant cell line which lacks the ability to grow independent of a supplemented media. Two examples are: CHO DHFR$^-$ cells and mouse LTK$^-$ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which are successfully transformed with a heterologous gene express a protein conferring drug resistance and thus survive the selection regimen. Examples of such dominant selection use the drugs neomycin (Southern et al., J. Molec. Appl. Genet. 1: 327 (1982)), mycophenolic acid (Mulligan et al., Science 209: 1422 (1980)) or hygromycin (Sugden et al., Mol. Cell. Biol. 5: 410-413 (1985)). The three examples given above employ bacterial genes under eukaryotic control to convey resistance to the appropriate drug G418 or neomycin (geneticin), xgpt (mycophenolic acid) or hygromycin, respectively.

Suitable eukaryotic host cells for expressing human DNase include monkey kidney CV1 line transformed by SV40 (COS-7, ATCC CRL 1651); human embryonic kidney line (293 or 293 cells subcloned for growth in suspension culture, Graham, F. L. et al., J. Gen Virol. 36: 59 [1977]); baby hamster kidney cells (BHK, ATCC CCL 10); chinese hamster ovary-cells-DHFR (CHO, Urlaub and Chasin, PNAS (USA) 77: 4216, [1980]); mouse sertoli cells (TM4, Mather, J. P., Biol. Reprod. 23: 243-251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather, J. P. et al., Annals N.Y. Acad. Sci. 383: 44-68 [1982]).

Construction of suitable vectors containing the desired coding and control sequences employ standard ligation techniques. Isolated plasmids or DNA fragments are cleaved, tailored, and religated in the form desired to form the plasmids required.

For analysis to confirm correct sequences in plasmids constructed, the ligation mixtures are used to transform *E. coli* K12 strain 294 (ATCC 31446) and successful transformants selected by ampicillin or tetracycline resistance where appropriate. Plasmids from the transformants are prepared, analyzed by restriction and/or sequenced by the method of Messing et al., Nucleic Acids Res. 9: 309 (1981) or by the method of Maxam et al., Methods in Enzymology 65: 499 (1980).

Host cells are transformed with the expression vectors of this invention and cultured in conventional nutrient media modified as appropriate for inducing promoters, selecting transformants or amplifying the DNase gene. The culture conditions, such as temperature, pH and the like, are those previously used with the host cell selected for expression, and will be apparent to the ordinarily skilled artisan.

"Transformation" means introducing DNA into an organism so that the DNA is replicable, either as an extrachromosomal element or by chromosomal integration. Unless indicated otherwise, the method used herein for transformation of the host cells is the method of Graham, F. and van der Eb, A., Virology 52: 456-457 (1973). However, other methods for introducing DNA into cells such as by nuclear injection or by protoplast fusion may also be used. If prokaryotic cells or cells which contain substantial cell wall constructions are used, the preferred method of transfection is calcium treatment using calcium chloride as described by Cohen, F. N. et al., Proc. Natl. Acad. Sci. (USA), 69: 2110 (1972).

"Transfection" refers to the introduction of DNA into a host cell whether or not any coding sequences are ultimately expressed. Numerous methods of transfection are known to the ordinarily skilled artisan, for example, $CaPO_4$ and electro-poration. Transformation of the host cell is the indicia of successful transfection.

DNase is recovered and purified from recombinant cell cultures by methods used heretofore with human, bovine, ovine, or porcine DNase, including ammonium sulfate or ethanol precipitation, acid extraction, anion or cation exchange chromatography, phosphocellulose chromatography, hydrophobic interaction chromatography, affinity chromatography (e.g. using DNA or nucleotides on a solid support), hydroxyapatite chromatography and lectin chromatography. Moreover, reverse-phase HPLC and chromatography using anti-DNase antibodies are useful for the purification of DNase. As noted previously, (Price et al., J. Biol. Chem. 244:917 [1969]) it is preferred to have low concentrations (approximately 0.1-5 mM) of calcium ion present during purification. Other divalent cations which stabilize DNase are also utilized. DNase may be purified in the presence of a protease inhibitor such as PMSF.

Human DNase is placed into therapeutic formulations together with required cofactors, and optionally is administered in the same fashion as has been the case for animal DNase such as bovine pancreatic DNase. The formulation of DNase may be liquid, and is preferably an isotonic salt solution such as 150 mM sodium chloride, containing 1.0 mM calcium at pH 7. The concentration of sodium chloride may range from 75-250 mM. The concentration of calcium may range from 0.01-5 mM, and other divalent cations which stabilize DNase may be included or substituted for calcium. The pH may range from 5.5-9.0, and buffers compatible with the included divalent cation may also be utilized. The formulation may be lyophilized powder, also containing calcium.

Commercially available nebulizers for liquid formulations, including jet nebulizers and ultrasonic nebulizers are useful for administration. Liquid formulations may be directly nebulized and lyophilized power nebulized after reconstitution. Alternatively, DNase may be aerosolized using a fluorocarbon formulation and a metered dose inhaler, or inhaled as a lyophilized and milled powder. In addition, the liquid formulation of DNase may be directly instilled in the nasotracheal or endotracheal tubes in intubated patients.

The purified DNase is employed for enzymatic alteration of the visco-elasticity or the stickiness of mucous. Human DNase is particularly useful for the treatment of patients with pulmonary disease who have abnormal, viscous or inspissated purulent secretions in conditions such as acute or chronic bronchopulmonary disease (infectious pneumonia, bronchitis or tracheobronchitis, bronchiectasis, cystic fibrosis, asthma, TB or fungal infections), atelectasis due to tracheal or bronchial impaction, and complications of tracheostomy. For such therapies a solution or finely divided dry preparation of human DNase is instilled in conventional fashion into the bronchi, e.g. by aerosolization of a solution of DNase. Human DNase is also useful for adjunctive treatment for improved management of abscesses or severe closed-space infections in conditions such as empyema, meningitis, abscess, peritonitis, sinusitis, otitis, periodontitis, pericarditis, pancreatitis, cholelithiasis, endocarditis and septic arthritis, as well as in topical treatments in a variety of inflammatory and infected lesions such as infected lesions of the skin and/or mucosal membranes, surgical wounds, ulcerative lesions and burns. Human DNase finds utility in maintaining the flow in medical conduits communicating with a body cavity, including surgical drainage tubes, urinary catheters, peritoneal dialysis ports, and intratracheal oxygen catheters. DNase may improve the efficacy of antibiotics in infections (e.g., gentamicin activity is markedly reduced by reversible binding to intact DNA). It also may be useful as an oral supplement in cases of pancreatic insufficiency. DNase will be useful in degrading DNA contaminants in pharmaceutical preparations: the preparation is contacted with DNase under conditions for degrading the contaminant DNA to oligonucleotide and thereafter removing the oligonucleotide and DNase from the preparation. Use of DNase immobilized on a water insoluble support is convenient in this utility. Finally, DNase may be useful in treating non-infected conditions in which there is an accumulation of cellular debris, including cellular DNA. For example, DNase would be useful after systemic administration in the treatment of pyelonephritis and tubulo-interstitial kidney disease (e.g., with blocked tubules secondary to cellular debris), including drug-induced nephropathy or acute tubular necrosis.

DNase may also be administered along with other pharmacologic agents used to treat the conditions listed above, such as antibiotics, bronchodilators, anti-inflammatory agents, and mucolytics (e.g. n-acetyl-cysteine). It may also be useful to administer DNase along with other therapeutic human proteins such as growth hormone, protease inhibitors, gamma-interferon, enkephalinase, lung surfactant, and colony stimulating factors.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be, known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8: 4057 (1980).

"Dephosphorylation" refers to the removal of the terminal 5' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation are conventional. Maniatis, T. et al., *Molecular Cloning* pp. 133-134 (1982). Reactions using BAP are carried out in 50 mM Tris at 68° C. to suppress the activity of any exonucleases which may be present in the enzyme preparations. Reactions were run for 1 hour. Following the reaction the DNA fragment is gel purified.

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T. et al., *Id.*, p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Filling" or "blunting" refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2-15 μg of the target DNA in 10 mM $MgCl_2$, 1 mM dithiothreitol, 50 mM NaCl, 10 mM Tris (pH 7.5) buffer at about 37° C. in the presence of 8 units of the Klenow fragment of DNA polymerase I and 250 μM of each of the four deoxynucleoside triphosphates. The incubation generally is terminated after 30 min. phenol and chloroform extraction and ethanol precipitation.

EXAMPLE 1

Cloning of Human Pancreatic DNase I cDNA Library Preparation

A human pancreatic cDNA library was constructed in λgt10 using polyadenylated mRNA prepared from freshly obtained and liquid $N_2$ frozen human pancreas (Lauffer et al., Nature 318:334 [1985]). Using oligo dT primers and EcoRI-SalI-XhoI-SstII adapters, a cDNA library of $0.9 \times 10^6$ independent isolates of greater than 600 bp was obtained.

Oligonucleotide Probes

Two long probes were synthesized based on the amino acid sequence of bovine DNase I. Two segments of amino acid sequence which exhibited low redundancy were selected and mammalian codon usage tables were employed.

```
Probe 1:
5' GTG-CTG-GAC-ACC-TAC-CAG-TAT-GAT-GAT-GGC-TGT-

GAG-TCC-TGT-GGC-AAT-GAC 3' (51 mer corresponding to the amino sequence Val-Leu-Asp-Thr-Tyr-Gln-Tyr- Asp-Asp-Gly-Cys-Glu-Ser-Cys-Gly-Asn-Asp)

Probe 2:
5' TAT-GAC-GTC-TAC-CTG-GAC-GTG-CAG-CAG-AAG-TGG-

CAT-CTG-AAT-GAT-GTG-ATG-CTG-ATG-GGC-GAC-TTC-AAC-

GC 3' (71 mer corresponding to the amino acid sequence Tyr-Asp-Val-Tyr-Leu-Asp-Val-Gln-Gln-Lys- Trp-His-Leu-Asn-Asp-Val-Met-Leu-Met-Gly-Asp-Phe- Asn)
```

Isolation of Human DNase I cDNA Clones

The two probes were end-labeled with T4 polynucleotide kinase and [$^{32}$P]adenosine triphosphate (Maniatis et al., Molecular Cloning, [Cold Spring Harbor Laboratory, 1982]), and used separately to screen the human pancreatic cDNA library under low stringency hybridization conditions: 20% formamide, 5× SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C. Low stringency washes were carried out in 1× SSC and 0.1% SDS at 42° C. Three (1, 2, and 6) of 600,000 clones hybridized with both probes and contained 1.3 kB inserts. These were subcloned into M13 vectors (Messing et al., Nucleic Acids Res. 9:309 [1981]) and sequenced by the chain-termination method (Sanger et al., J. Mol. Biol. 143:161 [1980]).

Comparison of the deduced amino acid sequence of clone 6 with the amino acid sequence of bovine pancreatic DNase I revealed extensive homology. Notable, however, was a large deletion and a large insertion in the deduced amino acid sequence of clone 6. In addition the insertion contained a stop at its termination and had the characteristics of a retained intron due to a misspliced message. Clones 1 and 2 also contained the putative intron.

Two additional exact nucleotide probes from the sequence of clone 6 were synthesized for obtaining additional clones.

```
Probe 4 (N-terminal probe):
5' CTG-AAG-ATC-GCA-GCC-TTC-AAC-ATC-CAG-ACA-TTT-

GGG-GAG-ACC (42 mer)

Probe 5 (putative intron probe):
5' TCC-GCA-TGT-CCC-AGG-GCC-ACA-GGC-AGC-GTT-TCC- TGG-TAG-GAC (42 mer)
```

The probes were labeled with $^{32}$P and used to rescreen $1.3 \times 10^6$ clones from the human pancreatic cDNA library at high stringency: 50% formamide, 5× SSC (0.75 M NaCl, 0.075 M sodium citrate), 50 mM sodium phosphate (pH 6.8), 0.1% sodium pyrophosphate, 5× Denhardt's, sonicated salmon sperm DNA (50 μg/ml), 0.1% SDS, and 10% dextran sulfate at 42° C. Washes were carried out at 42° C. in 0.2× SSC and 0.1% SDS. Four clones hybridized with probe 4 (N-terminal probe) and not with probe 5 (putative intron probe). Of these, clone 18-1, which contained an insert of approximately 1.1 kB by PAGE, was subcloned into M13 and sequenced. The full nucleotide sequence of clone 18-1 and the deduced amino acid sequence is shown in FIG. 1.

Clone 18-1 is composed of 1039 bp and has a long open reading frame without the intron found in clone 6. As noted, two possible initiation codons (ATG) are present (positions 160-162 and 169-171). Either may be used. The former ATG with a purine at position -3 more closely conforms to the Kozak rule (Kozak, Cell 44:283 [1986]). Between the putative initiation codons and the nucleotides corresponding to the N-terminal leucine (CTG at position 226-228 are nucleotides encoding a short, relatively hydrophobic amino acid sequence (19-22 amino acids in length) which is a likely secretion signal sequence.

Comparison of the deduced amino acid sequence of human DNase I with bovine DNase I reveals extensive amino acid homology (FIG. 2). The human and bovine proteins are 260 aa in length and possess an N-terminal leucine. The major structural features of the bovine protein, which include the four cysteines (101, 104, 173 and 209), the two potential N-linked glycosylation sites (18 and 106), and the active site histidine (134), are conserved. Overall there is approximately 77% amino acid identity.

The six regions of greatest amino acid diversity (amino acid residues 27-39, 83-96, 115-126, 156-161, 219-234 and 243-247) each contain more than three differences -and more than 54% of the amino acids are variable. Interestingly, these regions are also variable when the bovine sequence is compared with the ovine and porcine. Some of these regions are exposed loop structures according to the Xray crystal structure of bovine DNase (Oefner et al., J. Mol. Biol. 192:605 [1986]), and thus would be predicted to be relatively immunogenic. Thus, it is likely that the amino acid differences between the human and the bovine sequences may lead to immunologic reactions.

EXAMPLE 2

Assays for DNase Activity

In addition to standard ELISA (see example 4) and RIA, three assays have been developed to detect DNase activity.

1. Hydrolysis of $^{32}$P-labeled DNA. Radiolabeled $^{32}$P-DNA was prepared using an M13 single-stranded template, a 17 mer sequencing primer, $^{32}$P-dCTP, non-radioactive dATP, dTTP, and dGTP, and Klenow. Briefly, 1.5λ MgCl2 (35 mM), 1.5λ 10× restriction buffer (70 mM Tris-HCl, pH 7.6; 35 mM dithiothreitol; 1 mM EDTA), and 6λ H$_2$O were mixed with 1λ template (approximately 1 μg) and 1.5λ Palmer (0.5 μM) and heated to 55° C. for 7 min. Nucleotide mix was prepared by taking 40λ $^{32}$P-dCTP (sp. act.3000 Ci/mmol; 400 μCi) plus 1λ each of 2 mM stocks of non-radioactive dATP, dTTP, and dGTP to dryness and then reconstituting the nucleotides in 7μ 1× restriction buffer. The nucleotide mix and 1λ Klenow were added to the template-primer mixture and the reaction was incubated at 37° C. After 15 min, 2λ of a non-radioactive deoxynucleotides were added and the incubation was continued for an additional 15 min. Radiolabeled DNA was then separated from free nucleotides by centrifugation through Sephadex G-50 (Maniatis et al., [1982]).

DNase activity is measured by incubating samples with 100,000 cpm $^{32}$P-DNA plus 80 μg/ml non-radioactive salmon sperm DNA in DNase buffer (10 mM Tris-HCl pH7, 4 mM MgCl2, 4 mM CaCl2) for 45 min at 37° C. The reaction is terminated by the addition of one-half volume of non-radioactive DNA (2 mg/ml) and one volume of ice-cold 20% trichloroacetic acid. After 10 min at 4° C., the mixture is centrifuged at 12,000 g×10 min, and an aliquot of the supernatant is counted. The presence of acid-soluble counts in the supernatant reflects DNase activity. Each day a standard curve is generated by testing 0.1-200 ng of bovine DNase I (Sigma D-5025).

2. Agar plate DNase assay. Smith, Hankock, and Rhoden (Applied Microbiology, 18:991 [1969]) described a test agar containing methyl green and DNA for determining DNase activity of microorganisms. This assay was modified in order to develop a rapid semi-quantitative assay for soluble DNase activity in order to screen cell supernatants to monitor expression and to screen column fractions to monitor purification. To prepare the agar, bacto agar (7.5 g) is melted in 500 ml of buffer (25 mM Tris pH 7.5, 5 mM MgCl2, 5 mM CaCl2, 0.1% sodium azide). Salmon sperm DNA (1.0 g) and methyl green (17.5 mg) are added. After stirring for 1-2 hr at 55° C., and autoclaving, plates are poured and stored at 4° C. DNase activity is measured by spotting 0.5-5λ aliquots onto the plates, which are then incubated at room temperature or 37° C. for 4-48 hr. A standard curve is generated by aliquoting 0.1-1000 ng of bovine DNase I. DNase is readily measured by the size of the clear zones in the agar, there being a logarithmic relationship between DNase concentration and diameter of the clear zones. This assay format also is applicable for the rapid identification of high-expressing DNase-producing clones, either with a view towards producing DNase or towards screening transformants in which the DNase is used as a selectable marker or as a reporter gene.

In addition to using methyl green and DNA in an agar plate format, these reagents are also used in an aqueous format (e.g. in 96-well plates) to rapidly, sensitively, and specifically quantitate DNase activity.

3. SDS-polyacrylamide gel electrophoresis and xymography. SDS-polyacrylamide gel electrophoresis and xymography was performed by a modification of the procedure of Rosenthal and Lacks (Anal. Biochem. 80:76 [1977]). Briefly, the buffer system of Laemmli was used to prepare 12% polyacrylamide gels. Salmon sperm DNA (10 μg/ml) and EDTA (2 mM) were added to both the stacking and the resolving gels prior to polymerization. Proteins were suspended in sample buffer, heated at 100° C. for 3 min, prior to application to the gels. Electrophoresis was conducted at room temperature at constant current. Following electrophoresis, the gel was rinsed with water and incubated in 250 ml of 40 mM Tris-HCl, pH 7.5, 2. mM MgCL$_2$, 0.02% azide. After 1 hr, fresh buffer was added and the gel was soaked for 12 hr at 24° C. To reveal DNase activity, the gel was put into fresh buffer containing 2 mM CaCl2 and 1 µg/ml ethidium bromide, and then examined under short-wave UV light at intervals from 5 min to 24 hr. To stop the reaction EDTA is added (final concentration 15 mM), and the xymogram is photographed. The gel can then be stained for protein by Coomassie blue.

EXAMPLE 3

Expression of Human DNase I 1. pRK.DNase.7

Plasmid pRK.DNase.7 was constructed from clone 18-1, described above, as follows:

The plasmid pRK5 was digested with EcoRI, dephosphorylated, and fragment 1 comprising the bulk of the plasmid was isolated. pRK5 is described in Suva et al., *Science* 237:896 (1987); U.S. Ser. No. 97,472, filed Sep. 11, 1987; and EP Publ. 307,247, published 15 Mar. 1989, where the pCIS2.8c28D starting plasmid is described in EP 278,776 published Aug. 17, 1988 based on U.S. Ser. Nos. 07/071,674 and 06/907,297. The λ DNase clone 18-1 was digested with EcoRI and the insert (fragment 2) was isolated. Fragment 1 and fragment 2 were ligated and the ligation mixture transformed into *E. coli* strain 294. The transformed culture was plated on ampicillin media plates and resistant colonies selected. Plasmid DNA was prepared from transformants and checked by restriction analysis for the presence of the correct fragment.

pRK.DNase.7 was transfected into human embryonic kidney-293 cells for transient and stable expression. For transient expression of human DNase I, 60 mm plates of confluent HEK-293 cells (50%) were transfected as previously described (Eaton et al. 1986) by the calcium phosphate method (Wigler et al., 1979). For stable expression of human DNase I, HEK-293 cells were similarly transfected simultaneously with pRK.DNase.7 and a plasmid expressing the neomycin resistance gene pRSV neo (Gorman et al., 1985). Two days after transfection, the cells were passaged into standard medium (1:1 F12/DME supplemented with L-glutamine, penicillin-streptomycin and 10% FBS) with 0.5 mg/ml G418 (Genticin sulfate; Gibco) for selection of stable lines.

Analysis was undertaken of supernatants of 293 cells transfected either transiently or stably with the DNase plasmid revealed 0.2-1.0 µg/ml of DNase activity, as measured either by the 32P-DNA hydrolysis assay or the green agar plate DNase assay. Analysis of the transfected cell supernatants by SDS-PAGE and xymography revealed a new protein band at approximately 35-37 kD with DNase activity. Additional studies showed the recombinant human DNase I produced in 293 cells required calcium for activity, was inhibited by EDTA, heat, and actin, and had greater activity for double stranded DNA than for single stranded DNA. The specific activity of human DNase expressed in 293 cells appeared comparable to that of bovine DNase.

2. pSVeDNaseDHFR3 pSVeDNAseDHFR3, a plasmid suitable for recombinant synthesis of human DNase I in CHO cells was constructed as follows:

An intermediate plasmid was constructed in order to remove a redundant polylinker region. Plasmid pRK.D-Nase.7 was digested with EcoRI and SphI and the largest fragment containing the 5' portion of the DNase coding region was, isolated (fragment 3). Plasmid pRK.DNase.7 was digested with SalI, blunted with Klenow, digested with SphI, and the intermediate size fragment containing the 3' portion of the DNase coding region was isolated (fragment 4). pRK5 was cut with SmaI and EcoRI and the fragment comprising the bulk of the plasmid was isolated (fragment 5). Fragments 3, 4 and 5 were ligated and the mixture was transformed into *E. coli* strain 294. The transformed culture was plated on ampicillin media plates and resistant colonies selected. Plasmid DNA was prepared from transformants and checked by restriction analysis for the presence of the correct fragment. The resulting plasmid is referred to as pRKDNaseInt.

Plasmid pE342HBV.E400D22 (Crowley et al., "Mol. Cell Biol." 3:44 [1983]) was digested with EcoRI and PvuI and the smallest fragment containing the SV40 early promoter and part of the β-lactamase gene was isolated (fragment 5). Plasmid pE342HBV.E400D22 was also digested with BamHI and PvuI and the fragment comprising the bulk of the plasmid containing the balance of the β-lactamase gene as well as the SV40 early promoter and the DHFR gene was isolated (fragment 6). Plasmid pRKDNaseInt was digested with EcoRI and BamHI and the DNase coding fragment was isolated (fragment 7). Fragments 5, 6, and 7 were ligated and the mixture was transformed into *E. coli* strain 294. The transformed culture was plated on ampicillin media plates and resistant colonies selected. Plasmid DNA was prepared from transformants and checked by restriction analysis for the presence of the correct fragment. The resulting plasmid is referred to as pSVeDNaseDHFR3.

For stable expression of human DNase I, using the above plasmid, 60 mm plates of confluent CHO cells (DP-7) were transfected by the calcium phosphate method and grown initially in selective medium. Unamplified cell lines have grown out whose medium contains approximately 0.02-0.1 µg/ml of DNase activity, as measured either by the 32P-DNA hydrolysis assay or the green agar plate DNase assay. It is anticipated that higher levels (at least 5×) of expression would be achieved if these cells were grown to high density in a fermentor. Individual clones would be selected for their individual levels of DNase expression to pick high secreting cells, and thereafter amplifying each selected clone in the presence of increasing concentrations of MTX (12.5 to 2000 nM)

3. pDNA11

A plasmid was constructed suitable for recombinant synthesis of DNase in *E. coli* as a secreted protein. This plasmid is called pDNA11 and was constructed as follows.

Plasmid pTF.III (U.S. Ser. No. 07/152,698) was digested with NsiI and SalI and the largest fragment comprising the bulk of the plasmid was isolated (fragment 8). Plasmid pRKDNase7 was digested with SalI and BstXI and the 798 bp fragment comprising most of the coding region was isolated (fragment 9). Two synthetic oligonucleotides were synthesized:

DLink 1: 5'TTG-AAG-ATC-GCA-GCC-TTC-AAC-ATC-CAG-ACA-T (31 mer)

DLink 3: 5' CTG-GAT-GTT-GAA-GGV-TGC-GAT-CTT-CAA-TGC-A (31 mer)

Fragments 8 and 9 and synthetic oligonucleotides DLink 1 and DLink 3 were ligated and the mixture was transformed into *E. coli* strain 294. The transformed culture was plated on ampicillin media plates and resistant colonies selected. Plasmid DNA was prepared from transformants and checked by restriction analysis for the presence of the correct fragment and preservation of the NsiI and BstXI restriction sites. Several plasmids were sequenced to confirm incorporation of correct synthetic DNA. 294 cells transformed with pDNA11 expressed >500 mg/L of two new major proteins as revealed by SDS-PAGE—a major band at approximately 32 kD and a minor band at approximately 30 kD. Amino acid sequence analysis of the two bands revealed N-terminal sequences of Met-Lys-Lys-Asn-Ile-Ala and Leu-Lys-Ile-Ala-Ala-Phe, respectively. Thus, the higher MW band represents unprocessed human DNase and the lower MW band represents properly processed native human DNase.

Human DNase expressed in E. coli is active. 294 cells transformed with pDNA11 grown on agar plates supplemented with calcium, magnesium, and low phosphate revealed secretion of active DNase, as evidenced the presence of a clear zone surrounding the transformed cells, and not control cells. In addition, transformed cells solubilized with SDS and beta-mercaptoethanol were run into SDS-PAGE gels and xymography was performed. DNase activity was associated with the band of properly processed human DNase, but not with unprocessed human DNase.

4. pDNA2

A plasmid was constructed for recombinant expression of human DNase I as an intracellular protein in E. coli. The plasmid is called pDNA2, and was constructed as follows.

Plasmid pHGH207/307 was prepared from pHGH207 (U.S. Pat. No. 4,663,283) by removing the EcoRI site upstream from the trp promoter (EcoRI digested, blunted and religated).

Plasmid pHGH207/307 was digested with XbaI and SalI and the largest fragment comprising the bulk of the plasmid was isolated (fragment 10). Plasmid pRK.DNase.7 was digested with SalI and BstXI and the 798 bp fragment comprising most of the coding region was isolated (fragment 9). Two synthetic oligonucleotides were synthesized:

```
DLink 4:
5' CTAGAATTATG-TTA-AAA-ATT-GCA-GCA-TTT-AAT-ATT-

CAA-ACA-T (42mer)

DLink 5:
5' TTG-AAT-ATT-AAA-TGC-TGC-AAT-TTT-TAACATAATT (34mer)
```

Fragments 9 and 10 and synthetic oligonucleotides DLink 4 and DLink 5 were ligated and the mixture was transformed into E. coli strain 294. The transformed culture was plated on ampicillin media plates and resistant colonies selected. Plasmid DNA was prepared from transformants and checked by restriction analysis for the presence of the correct fragment and preservation of the XbaI and BstXI restriction sites. Several plasmids were sequenced to confirm incorporation of correct synthetic DNA.

294 cells transformed with pDNA2 expressed one new major protein as revealed by SDS-PAGE of approximately 30 kD. Amino acid sequence analysis of protein revealed N-terminal sequence Met-Leu-Lys-Ile-Ala-Ala-Phe, corresponding to human Met-DNase.

Human Met-DNase expressed directly in E. coli is also active. Transformed cells solubilized with SDS and beta-mercaptoethanol were run into SDS-PAGE gels and xymography was performed. DNase activity was associated with the band of human Met-DNase.

EXAMPLE 4

Further Analysis of DNase Expression a. DNase Expression Vectors

The human pancreatic deoxyribonuclease (DNase) I cDNA from plasmid pRK.DNase.7 described above, which contains the entire insert from DNase cDNA clone 18-1 isolated from a λgt10 human pancreatic cDNA library in vector pRK5, was transferred into pRK5 to create the intermediate expression vector pRK.DNase.3. In this plasmid (pRK.DNase.3), DNase synthesis is directed by the CMV transcription regulatory elements. A splice unit, described below, is located between the transcription and translation initiation sites. For generation of DNAse expression vectors, the CMV transcription regulatory sequences and the splice unit of pRK.DNase.3 were replaced by the SV40 transcription regulatory sequences and different splice donor-intron-splice acceptor units as described below. For comparison, a corresponding vector lacking the splice unit was also created (pSve.DNase).

1. pRK.DNase.3

Vector pRK.DNase.3 (FIG. 3) was constructed as follows: pRK5 was digested with SmaI and SalI, which cut exclusively in the polylinker region between the 5' and 3' control sequences, and the large fragment was isolated. The pRK5 vector contains a splice donor-intron-splice acceptor region upstream of a coding region and downstream of a promoter, where the intron region consists of a cytomegalovirus (CMV) immediate early splice donor and intron sequences, a bacteriophage SP6 promoter insert, and immunoglobulin (Ig) heavy chain variable region ($V_H$) intron and splice acceptor sequences. Vector pRK.DNase.7 was cleaved with BsmI, the 3' protruding ends were trimmed back with T4 DNA polymerase, and the material was redigested with SalI to release the entire human DNase I coding sequence as a 921-nt fragment. After gel isolation, this fragment was ligated to the pRK5 large fragment using standard ligation methodology (Maniatis et al., 1982, supra) to create vector pRK.DNase.3.

pRK.DNase.3 contains CMV transcription regulatory elements, and a splice unit located between the transcription and translation initiation sites ("Intron" in FIG. 3). In this vector, the splice unit of the pRK5 vector is present without any modifications.

2. pSVe.DNase

Vector pSVe.DNase was constructed as follows (FIG. 3): The regulatory sequences preceding the DNAse coding region in vector pRK.DNase.3 were separated from the remainder of the vector by digestion with SstI and ClaI; DNA prepared from dam$^+$ bacterial host cells was used to prevent cleavage of the second ClaI site in the vector, located towards the 3' end of the SV40 early polyadenylation region. The largest fragment lacking the 5' control region was gel isolated.

DHFR expression vector pE348DHFRUC served as a source of the SV40 transcription regulatory sequences. The vector pE348DHFRUC (Vannice and Levinson, J. Virology, 62:1305-1313, 1988, where it is designated pE, FIG. 1) contains the SV40 enhancer and early promoter region upstream of the HindIII site, including the SV40 early sties of transcription initiation (position 5171 in the virus), preceding cDNA encoding murine dihydrofolate reductase (DHFR), which is followed by the 584-bp Hepatitis B virus (HBV) polyA signal in plasmid pML1 from the GamHI to the BGIII sites of HBV. This plasmid contains a polylinker immediately upstream of the SV40 sequences. The SV40 transcription regulatory sequences, were released by digestion with SstI and ClaI, and the resulting 5' protruding ends were filled in using Klenow polI in the presence of all four deoxyribonucleotides (dNTPs: dATP, dGTP, dCTP, TTP). Upon subsequent digestion with XbaI, the SV40 transcription regulatory sequences (enhancer and early promoter, including the SV40 early sites of transcription initiation), present on the smaller XbaI-ClaI fragment (360 nucleotides) were gel isolated.

The smaller fragment from pE34DHFRUC described immediately above was gel isolated and ligated to the large pRK.DNase.3 fragment to generate vector pSVe.DNase. In this vector, DNase synthesis is directed by the SV40 transcription control sequences, but no splice unit is present between these and the DNase coding region.

3. pSVI.DNase

Figure 4:
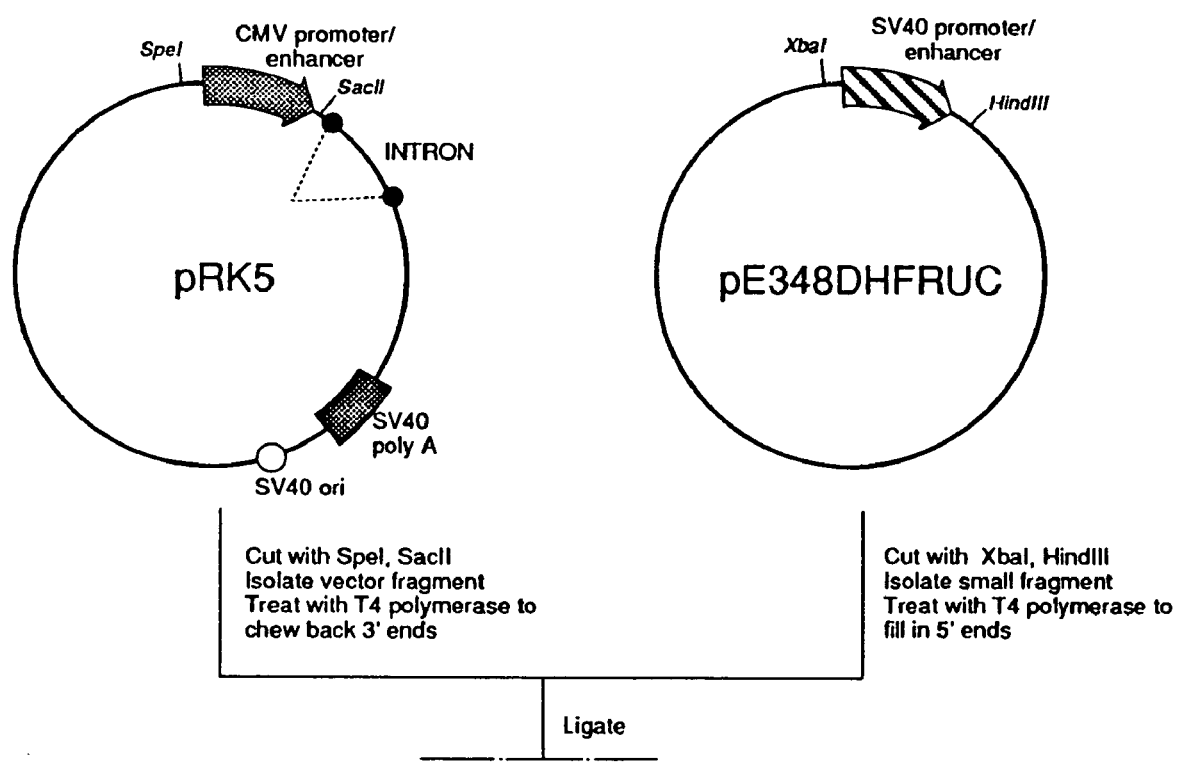
FIG. 4 shows the construction of the expression vector pSVI.DNase that contains the splice unit of the pRK5 vector without any modifications.
Figure 4:
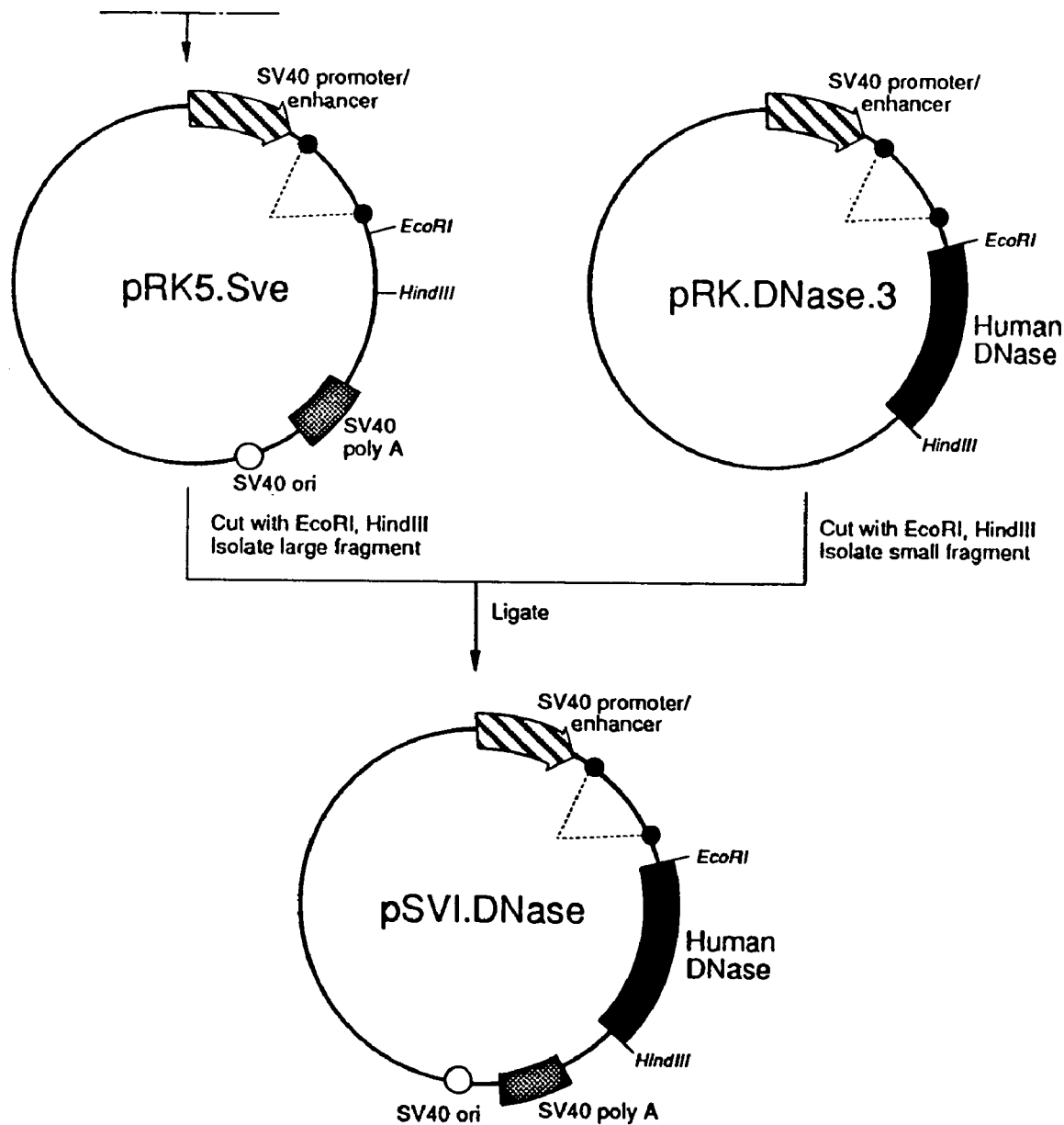

Vector pSVI.DNase (FIG. 4) was prepared after insertion of the DNase coding sequence into an intermediate plasmid, pRK5.SVe. This intermediate was created by replacing the pRK5 CMV transcription regulatory elements, located between SpeI and SacII restriction sites, with the small XbaI-HindIII fragment from pE348DHFRUC that contains the SV40 early promoter and enhancer. The 3' protruding ends generated by SacII digestion of pRK5 were chewed back with T4 DNA polymerase, and the 5' protruding ends resulting from HindIII digestion of pE348DHFRUC were filled in using T4 polymerase in the presence of all four dNTPs.

For construction of pSVI.DNase, the DNase coding sequence was isolated from vector pRK.DNase.3 by cleavage with EcoRI and HindIII, and inserted into the large fragment of pRK5.Sve that had been isolated after digestion with the same two enzymes. Vector pSVI.DNase contains the SV40 transcription regulatory elements (enhancer and early promoter, including the SV40 early sites of transcription initiation) and mRNA cap sites, followed by the splice-donor-intron-splice acceptor unit of the pRK5 vector without any modifications, the cDNA encoding DNase, the SV40 early polyadenylation ("polyA") region, and the SV40 origin of replication ("ori") regions from SV40.

The complete nucleotide sequence of pSVI.DNase up to, but not including, the coding region of DNase is shown in FIG. 6.

4. pSVI2, DNase, pSVI3, DNase, pSVI5, DNase, and pSVI6B, DNase

Figure 5:
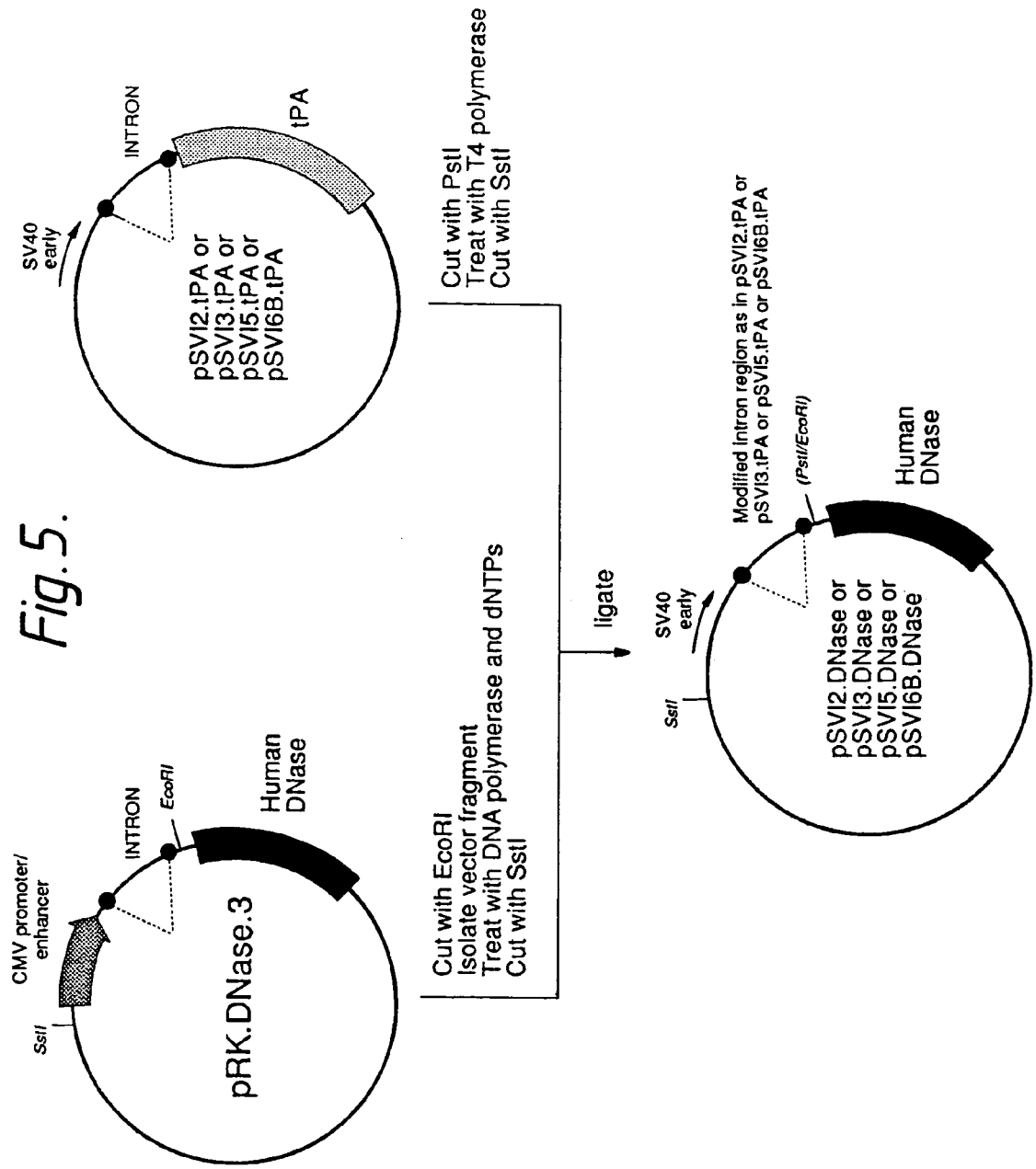
FIG. 5 shows the construction of the expression vectors pSVI2.DNase, pSVI3.DNase, pSVI5.DNase, and pSVI6b.DNase containing the modifications in the splice unit and surrounding DNA.

Vectors pSVI2.DNase, pSVI3.DNase, pSVI5.DNase, and pSVI6B.DNase were constructed (FIG. 5) by recombining two fragments in each case. The first was the large pRK.DNase.3 fragment resulting from digestion with EcoRI, treatment with T4 DNA polymerase in the presence of dNTPs, and subsequent cleavage with SstI; the second was in each case the small fragment containing the SV40 5' regulatory sequences and a modified splice unit.

Figure 11:
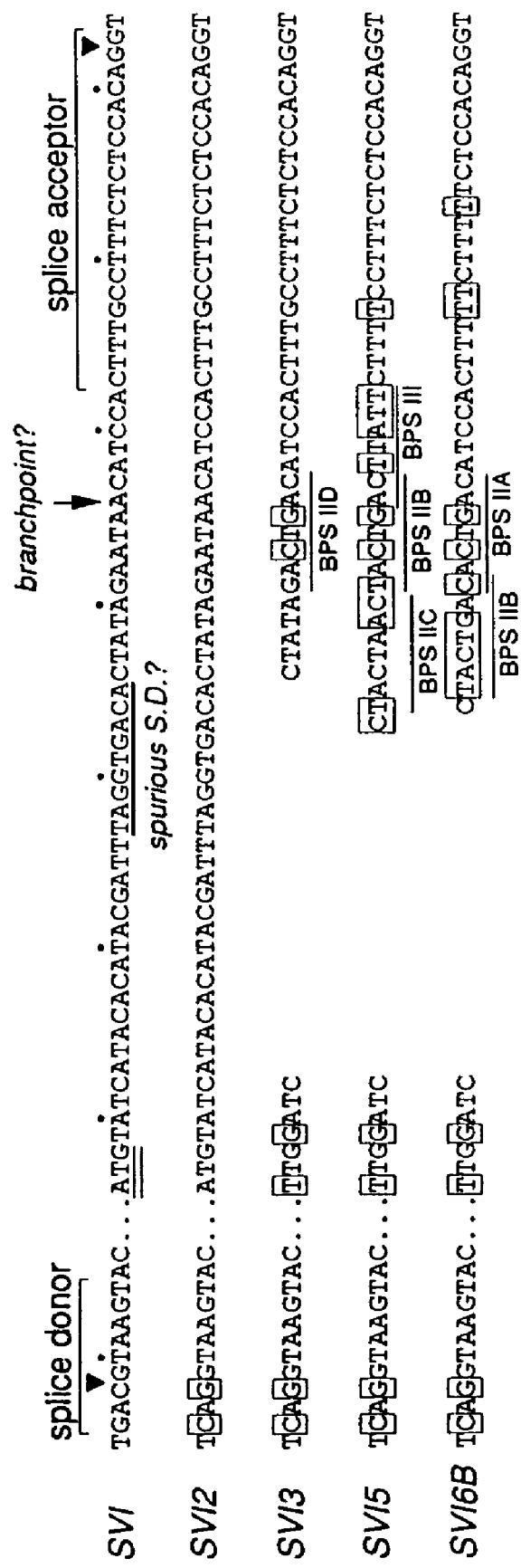
FIG. 11 shows a schematic representation of the splice unit nucleotide sequences involved in the preparation of the vectors of this example, i.e., SVI, SVI2, SVI3, SVI5, and SVI6B. The boxes represent changes from the SVI sequence, the double underlining is a spurious ATG codon, the underlining shows spurious splice sites and added or changed branchpoint sequence (BPS) regions, the breaks in sequence represent deletions of the nucleotides for SVI3-SVI5, the " . . . " designation indicates sequence not shown, and the carets indicate the 5' and 3' cleavage sites within the splice donor and splice acceptor, respectively, of the splice unit.

Modifications to splice units for enhancing recombinant expression in mammalian cells are described in a copending application filed 3 Dec. 1989, given U.S. Ser. No. 07/448, 038, specifically incorporated herein by reference. FIG. 11 shows a schematic representation of the splice unit nucleotide sequences involved in the preparation of the vectors of this example, i.e., SVI, SVI2, SVI3, SVI5, and SVI6B. The boxes represent changes from the SVI sequence, the double underlining is a spurious ATG codon, the underlining shows spurious splice sites and added or changed branchpoint sequence (BPS) regions, the breaks in sequence represent deletions of the nucleotides for SVI3-SVI5, the " . . . " designation indicates sequence not shown, and the carets indicate the 5' and 3' cleavage sites within the splice donor and splice acceptor, respectively, of the the splice unit. These sequences may be prepared by known methods of protein synthesis, or by standard modifications of the pSVI sequence, or by the method of U.S. Ser. No. 07/448,038, id.

FIGS. 7-10 show the complete nucleotide sequences of pSVI2.DNase, pSVI3.DNase, pSVI5.DNase, and pSVI6B.DNase, respectively, up to but not including the coding region of DNase. The splice unit sequences of FIG. 11 are incorporated in FIGS. 7-10.

b. Transient DNase Expression

Transient expression directed by the different DNase vectors was analyzed after transfection into CHO dhfr⁻ cells. Cells were transfected by a modification of the DEAE-dextran procedure and levels of DNase accumulated in the cell media 36 to 48 hours after transfection. Approximately $4 \times 10_5$ cells were plated per well in six-well 35 mm culture dishes. The following day, the volume of 2 μg DNase expression vector was adjusted to 15 μl by the addition of TBS (137 mM NaCl, 5 mM KCl, 1.4 mM $Na_2PO_4$, 24.7 mM TrisHCl, 1.35 mM $CaCl_2$, 1.05 MM $MgCl_2$, pH 7.5). 30 μl DEAE-dextran (10/mg/ml) and 2 ml serum-free culture medium containing 100 μM chloroquine were then added. The cell media was removed, the cells were rinsed once with PBS (phosphate buffered saline, pH 7.5), and the DNA mixture was added. This was followed two to three hours later by a glycerol shock, and the cells were covered with 2 ml regular growth media until assayed. The DNase vectors were cotransfected with 2 μg of a control plasmid, pRS-V.hGH, which directs expression of the human growth hormone (hGH) gene controlled by the transcription regulatory sequences in the long terminal repeat (LTR) of Rous sarcoma virus. This plasmid may be prepared by replacing the ras promoter of rasP.hGH described in Cohen and Levinson, *Nature,* 334: 119-124 (1988) with the RSV promoter. The amount of hGH synthesized in each case served as a standard to allow for a more precise comparison of the DNase levels obtained in the different transfections. Shown below are the levels of DNase and hGH produced in a typical experiment performed in duplicate:

| Vector | ng/ml DNase | | ng/ml hGH | | (corrected) ng/ml DNase | |
|---|---|---|---|---|---|---|
| | run1 | run2 | run1 | run2 | run1 | run2 |
| pSVe.DNase | 19.7 | 17.4 | 50.1 | 42.0 | 8.6 | 9.2 |
| pSVI.DNase | 17.9 | 13.8 | 29.7 | 20.4 | 12.8 | 14.7 |
| pSVI2.DNase | 34.2 | 30.5 | 41.9 | 40.3 | 18.0 | 17.0 |
| pSVI3.DNase | 37.8 | 28.7 | 45.2 | 40.5 | 18.0 | 15.1 |
| pSVI5.DNase | 28.4 | 22.1 | 37.2 | 28.7 | 16.7 | 17.0 |
| pSVI6B.DNase | 28.5 | 37.8 | 61.3 | 67.5 | 10.2 | 12.2 |

DNase levels in the media were measured by a standard ELISA using serum from rabbits injected either with human DNase or bovine DNase and adjuvant (*Practice and Theory of Enzyme Immunoassays,* P. Tijssen, Chapter 5, "Production of antibodies", pg. 43-78 (Elsevier, Amsterdam 1985)). hGH levels were determined using a commercially available assay kit (IRMA, immunoradiometric assay) purchased from Hybritech, Inc., La Jolla, Calif.

The data in the last column suggest that DNase expression directed by vectors pSVI2.DNase, pSVI3.DNase, and pSVI5.DNase is somewhat higher than that obtained with the parental vector pSVI.DNase. The numbers in the first column show more significant differences that now apply also to pSVI6B.DNase. Although it would appear that the third column presents the more credible set of data, it is not certain that efficient hGH synthesis does not adversely affect the level of DNase synthesis. For example, without limitation to any one theory, expression at this level may likely cause competition for components in the secretory pathway, and as a result a reduced DNase level when hGH expression is high. Other competitive effects may also bias the results such that the first column of data may well represent the actual differences in expression capability among the various DNase vectors. In either case, it is clear that at least some of the vectors containing a modified splice unit express higher levels of DNase in a transient assay than the corresponding vector that has the original splice unit.

c. Stable DNase Expression

2 µg of plasmid pSVe.DNase, pSVI.DNase, pSVI2.DNase, pSVI3.DNase, pSVI5.DNase, or pSVI6B.DNase were transfected into CHO-dhfr⁻ cells in a 60-mm dish with 0.1 µg of pFD11. After two days the cells were split 90% and 10% in 10-cm dishes. When colonies appeared, they were counted and assayed as mixed colonies. Per cell assays were performed in duplicate (designated A or B in the table below), except for pSVI2.DNase which was measured once. In this assay, the cell line was set up at $2\times10^5$ cells/well-6 well dish in 3 ml. Three days later cells were counted and the media was assayed for DNase using the DNase ELISA described above with a range of 0.2 to 25 ng/ml. The results are indicated below:

| | pg/cell/day DNase | |
| Vector | A | B |
| --- | --- | --- |
| pSVe.DNase | 0.057 | 0.040 |
| pSVI.DNase | 0.079 | 0.016 |
| pSVI2.DNase | 0.067 | |

| | pg/cell/day DNase | |
| Vector | A | B |
| --- | --- | --- |
| pSVI3.DNase | 0.048 | 0.043 |
| pSVI5.DNase | 0.014 | 0.005 |
| pSVI6B.DNase | 0.039 | 0.062 |

EXAMPLE 5

Reduction in Viscosity of Purulent Sputum by Recombinant Human DNase

The effects of recombinant human DNase I and pure bovine DNase I (Worthington) on purulent sputum produced by a patient with cystic fibrosis was examined using a simple pourability assay. Briefly, samples were incubated with approximately 100 µl of sputum in Eppendorf test tubes. After various periods of time at 37° C., the tubes were inverted and the ability of the sputum to pour down the side of a test tube was evaluated on a scale of 0 (no movement) to 5+ (free-flowing down the side of the tube). Whereas 293 supernatants from human DNase I transfected cells caused a change of 4-5+ after 30 min incubation, untransfected cell supernatants had no effect. The specificity was confirmed by showing that EDTA—which inhibits bovine and human DNase—completely prevented the 293 supernatants from human DNase I transfected cells from liquefying cystic fibrosis sputum. In addition, the effects on sputum of bovine DNase which was pure and free of proteases was examined for the first time. Previously published reports all utilized bovine DNase which acknowledged to be contaminated with significant quantities of chymotrypsin and trypsin, proteins which had been shown to have activity on sputum by themselves. Pure bovine DNase I, free of proteases, rapidly liquified purulent sputum. Thus, pure DNase alone is effective at reducing the viscosity of sputum.

The invention claimed is:

1. A DNA isolate encoding a human DNase polypeptide comprising the amino acid sequence shown in FIG. 1 for mature human DNase or a variant thereof, in which the amino acid at position 140 of the mature human DNase is alanine.

2. The isolate of claim 1 wherein the isolate is free of DNase introns.

3. The isolate of claim 1 wherein the isolate is free of genomic DNA which encodes another polypeptide from the source of the DNA.

4. The isolate of claim 1, wherein the DNA encodes a polypeptide having the amino acid sequence shown in FIG. 1 for mature human DNase wherein the amino acid at position 140 of the mature human DNase is alanine.

5. A recombinant expression vector comprising the DNA isolate of claim 4.

6. A composition comprising a cell transformed with the recombinant expression vector of claim 5.

7. The composition of claim 6 wherein the cell is a mammalian cell.

8. A process for producing DNase which comprises transforming a host cell with a vector according to claim 5, culturing the transformed cell and recovering DNase from the culture.

9. The process according to claim 8 wherein the DNase is recovered from the culture medium of the host cell.

10. The process according to claim 9 wherein the host cell is a eukaryotic cell.

11. The process of claim 10 wherein the eukaryotic cell is a human embryonic kidney cell line.

12. The process of claim 10 wherein the DNase is secreted into the culture medium.

* * * * *

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 51 base pairs
      (B) TYPE: Nucleic Acid
      (C) STRANDEDNESS: Single
      (D) TOPOLOGY: Linear (xi) SEQUENCE DESCRIPTION: SEQ ID NO: 1:

```
GTGCTGGACA CCTACCAGTA TGATGATGGC TGTGAGTCCT GTGGCAATGA            50

C                                                                 51
```

(2) INFORMATION FOR SEQ ID NO: 2:

(i) SEQUENCE CHARACTERISTICS:
      (A) LENGTH: 17 amino acids
      (B) TYPE: Amino Acid (D) TOPOLOGY: Linear (xi) SEQUENCE DESCRIPTION: SEQ ID NO: 2:

Val Leu Asp Thr Tyr Gln Tyr Asp Asp Gly Cys Glu Ser Cys Gly
 1               5                  10                  15

Asn Asp (2) INFORMATION FOR SEQ ID NO: 3:

(i) SEQUENCE CHARACTERISTICS:
        (A) LENGTH: 71 base pairs
        (B) TYPE: Nucleic Acid
        (C) STRANDEDNESS: Single
        (D) TOPOLOGY: Linear (xi) SEQUENCE DESCRIPTION: SEQ ID NO: 3:

TATGACGTCT ACCTGGACGT GCAGCAGAAG TGGCATCTGA ATGATGTGAT            50

GCTGATGGGC GACTTCAACG C                                          71

(2) INFORMATION FOR SEQ ID NO: 4:

(i) SEQUENCE CHARACTERISTICS:
        (A) LENGTH: 23 amino acids
        (B) TYPE: Amino Acid
        (D) TOPOLOGY: Linear (xi) SEQUENCE DESCRIPTION: SEQ ID NO: 4:

Tyr Asp Val Tyr Leu Asp Val Gln Gln Lys Trp His Leu Asn Asp
 1               5                  10                  15

Val Met Leu Met Gly Asp Phe Asn
                20

(2) INFORMATION FOR SEQ ID NO: 5:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO: 5:

CTGAAGATCG CAGCCTTCAA CATCCAGACA TTTGGGGAGA CC                    42

(2) INFORMATION FOR SEQ ID NO: 6:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO: 6:

TCCGCATGTC CCAGGGCCAC AGGCAGCGTT TCCTGGTAGG AC                    42

(2) INFORMATION FOR SEQ ID NO: 7:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO: 7:

TTGAAGATCG CAGCCTTCAA CATCCAGACA T                                31

(2) INFORMATION FOR SEQ ID NO: 8:

(i) SEQUENCE CHARACTERISTICS:
        (A) LENGTH: 31 base pairs
        (B) TYPE: Nucleic Acid
        (C) STRANDEDNESS: Single
        (D) TOPOLOGY: Linear (xi) SEQUENCE DESCRIPTION: SEQ ID NO: 8:

```
CTGGATGTTG AAGGVTGCGA TCTTCAATGC A                              31
```

(2) INFORMATION FOR SEQ ID NO: 9:

(i) SEQUENCE CHARACTERISTICS:
        (A) LENGTH: 42 base pairs
        (B) TYPE: Nucleic Acid
        (C) STRANDEDNESS: Single
        (D) TOPOLOGY: Linear (xi) SEQUENCE DESCRIPTION: SEQ ID NO: 9:

```
CTAGAATTAT GTTAAAAATT GCAGCATTTA ATATTCAAAC AT                  42
```

(2) INFORMATION FOR SEQ ID NO: 10:

(i) SEQUENCE CHARACTERISTICS:
        (A) LENGTH: 34 base pairs
        (B) TYPE: Nucleic Acid
        (C) STRANDEDNESS: Single
        (D) TOPOLOGY: Linear (xi) SEQUENCE DESCRIPTION: SEQ ID NO: 10:

```
TTGAATATTA AATGCTGCAA TTTTTAACAT AATT                           34
```

(2) INFORMATION FOR SEQ ID NO: 11:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 11:

```
Met Leu Lys Ile Ala Ala Phe
 1               5
```

(2) INFORMATION FOR SEQ ID NO: 12:

(i) SEQUENCE CHARACTERISTICS:
        (A) LENGTH: 1039 base pairs
        (B) TYPE: Nucleic Acid
        (C) STRANDEDNESS: Double
        (D) TOPOLOGY: Linear (xi) SEQUENCE DESCRIPTION: SEQ ID NO: 12:

```
TCCTGCACAG GCAGTGCCTT GAAGTGCTTC TTCAGAGACC TTTCTTCATA          50
GACTACTTTT TTTTCTTTAA GCAGCAAAAG GAGAAAATTG TCATCAAAGG         100
ATATTCCAGA TTCTTGACAG CATTCTCGTC ATCTCTGAGG ACATCACCAT         150
CATCTCAGGA TGAGGGGCAT GAAGCTGCTG GGGGCGCTGC TGGCACTGGC         200
GGCCCTACTG CAGGGGGCCG TGTCCCTGAA GATCGCAGCC TTCAACATCC         250
AGACATTTGG GGAGACCAAG ATGTCCAATG CCACCCTCGT CAGCTACATT         300
GTGCAGATCC TGAGCCGCTA TGACATCGCC CTGGTCCAGG AGGTCAGAGA         350
CAGCCACCTG ACTGCCGTGG GGAAGCTGCT GGACAACCTC AATCAGGATG         400
```

-continued

```
CACCAGACAC CTATCACTAC GTGGTCAGTG AGCCACTGGG ACGGAACAGC         450

TATAAGGAGC GCTACCTGTT CGTGTACAGG CCTGACCAGG TGTCTGCGGT         500

GGACAGCTAC TACTACGATG ATGGCTGCGA GCCCTGCGGG AACGACACCT         550

TCAACCGAGA GCCAGCCATT GTCAGGTTCT TCTCCCGGTT CACAGAGGTC         600

AGGGAGTTTG CCATTGTTCC CCTGCATGCG GCCCCGGGGG ACGCAGTAGC         650

CGAGATCGAC GCTCTCTATG ACGTCTACCT GGATGTCCAA GAGAAATGGG         700

GCTTGGAGGA CGTCATGTTG ATGGGCGACT TCAATGCGGG CTGCAGCTAT         750

GTGAGACCCT CCCAGTGGTC ATCCATCCGC CTGTGGACAA GCCCCACCTT         800

CCAGTGGCTG ATCCCCGACA GCGCTGACAC CACAGCTACA CCCACGCACT         850

GTGCCTATGA CAGGATCGTG GTTGCAGGGA TGCTGCTCCG AGGCGCCGTT         900

GTTCCCGACT CGGCTCTTCC CTTTAACTTC CAGGCTGCCT ATGGCCTGAG         950

TGACCAACTG GCCCAAGCCA TCAGTGACCA CTATCCAGTG GAGGTGATGC        1000

TGAAGTGAGC AGCCCCTCCC CACACCAGTT GAACTGCAG                    1039
```

(2) INFORMATION FOR SEQ ID NO: 13:

(i) SEQUENCE CHARACTERISTICS:
        (A) LENGTH: 341 amino acids
        (B) TYPE: Amino Acid
        (D) TOPOLOGY: Linear (xi) SEQUENCE DESCRIPTION: SEQ ID NO: 13:

```
Ser Cys Thr Gly Ser Ala Leu Lys Cys Phe Arg Asp Leu Ser
 1               5                  10                  15

Ser Thr Thr Phe Phe Ser Leu Ser Ser Lys Arg Arg Lys Leu Ser
                20                  25                  30

Ser Lys Asp Ile Pro Asp Ser Gln His Ser Arg His Leu Gly His
                35                  40                  45

His His His Leu Arg Met Arg Gly Met Lys Leu Leu Gly Ala Leu
                50                  55                  60

Leu Ala Leu Ala Ala Leu Leu Gln Gly Ala Val Ser Leu Lys Ile
                65                  70                  75

Ala Ala Phe Asn Ile Gln Thr Phe Gly Glu Thr Lys Met Ser Asn
                80                  85                  90

Ala Thr Leu Val Ser Tyr Ile Val Gln Ile Leu Ser Arg Tyr Asp
                95                 100                 105

Ile Ala Leu Val Gln Glu Val Arg Asp Ser His Leu Thr Ala Val
               110                 115                 120

Gly Lys Leu Leu Asp Asn Leu Asn Gln Asp Ala Pro Asp Thr Tyr
               125                 130                 135

His Tyr Val Val Ser Glu Pro Leu Gly Arg Asn Ser Tyr Lys Glu
               140                 145                 150

Arg Tyr Leu Phe Val Tyr Arg Pro Asp Gln Val Ser Ala Val Asp
               155                 160                 165

Ser Tyr Tyr Tyr Asp Asp Gly Cys Glu Pro Cys Gly Asn Asp Thr
               170                 175                 180

Phe Asn Arg Glu Pro Ala Ile Val Arg Phe Phe Ser Arg Phe Thr
               185                 190                 195

Glu Val Arg Glu Phe Ala Ile Val Pro Leu His Ala Ala Pro Gly
               200                 205                 210

Asp Ala Val Ala Glu Ile Asp Ala Leu Tyr Asp Val Tyr Leu Asp
```

```
                   215                 220                 225
Val Gln Glu Lys Trp Gly Leu Glu Asp Val Met Leu Met Gly Asp
               230                 235                 240

Phe Asn Ala Gly Cys Ser Tyr Val Arg Pro Ser Gln Trp Ser Ser
               245                 250                 255

Ile Arg Leu Trp Thr Ser Pro Thr Phe Gln Trp Leu Ile Pro Asp
               260                 265                 270

Ser Ala Asp Thr Thr Ala Thr Pro Thr His Cys Ala Tyr Asp Arg
               275                 280                 285

Ile Val Val Ala Gly Met Leu Leu Arg Gly Ala Val Val Pro Asp
               290                 295                 300

Ser Ala Leu Pro Phe Asn Phe Gln Ala Ala Tyr Gly Leu Ser Asp
               305                 310                 315

Gln Leu Ala Gln Ala Ile Ser Asp His Tyr Pro Val Glu Val Met
               320                 325                 330

Leu Lys Ala Ala Pro Pro His Thr Ser Thr Ala
               335                 340

(2) INFORMATION FOR SEQ ID NO: 14:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO: 14:

Leu Lys Ile Ala Ala Phe Asn Ile Gln Thr Phe Gly Glu Thr Lys
 1               5                  10                  15

Met Ser Asn Ala Thr Leu Val Ser Tyr Ile Val Gln Ile Leu Ser
                20                  25                  30

Arg Tyr Asp Ile Ala Leu Val Gln Glu Val Arg Asp Ser His Leu
                35                  40                  45

Thr Ala Val Gly Lys Leu Leu Asp Asn Leu Asn Gln Asp Ala Pro
                50                  55                  60

Asp Thr Tyr His Tyr Val Val Ser Glu Pro Leu Gly Arg Asn Ser
                65                  70                  75

Tyr Lys Glu Arg Tyr Leu Phe Val Tyr Arg Pro Asp Gln Val Ser
                80                  85                  90

Ala Val Asp Ser Tyr Tyr Tyr Asp Asp Gly Cys Glu Pro Cys Gly
                95                 100                 105

Asn Asp Thr Phe Asn Arg Glu Pro Ala Ile Val Arg Phe Phe Ser
               110                 115                 120

Arg Phe Thr Glu Val Arg Glu Phe Ala Ile Val Pro Leu His Ala
               125                 130                 135

Ala Pro Gly Asp Ala Val Ala Glu Ile Asp Ala Leu Tyr Asp Val
               140                 145                 150

Tyr Leu Asp Val Gln Glu Lys Trp Gly Leu Glu Asp Val Met Leu
               155                 160                 165

Met Gly Asp Phe Asn Ala Gly Cys Ser Tyr Val Arg Pro Ser Gln
               170                 175                 180

Trp Ser Ser Ile Arg Leu Trp Thr Ser Pro Thr Phe Gln Trp Leu
               185                 190                 195

Ile Pro Asp Ser Ala Asp Thr Thr Ala Thr Pro Thr His Cys Ala
               200                 205                 210

Tyr Asp Arg Ile Val Val Ala Gly Met Leu Leu Arg Gly Ala Val
```

```
                        215                 220                 225
Val Pro Asp Ser Ala Leu Pro Phe Asn Phe Gln Ala Ala Tyr Gly
                230                 235                 240

Leu Ser Asp Gln Leu Ala Gln Ala Ile Ser Asp His Tyr Pro Val
                245                 250                 255

Glu Val Met Leu Lys
                260

(2) INFORMATION FOR SEQ ID NO: 15:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO: 15:

Leu Lys Ile Ala Ala Phe Asn Ile Arg Thr Phe Gly Glu Thr Lys
 1               5                  10                  15

Met Ser Asn Ala Thr Leu Ala Ser Tyr Ile Val Arg Ile Val Arg
                20                  25                  30

Arg Tyr Asp Ile Val Leu Ile Glu Gln Val Arg Asp Ser His Leu
                35                  40                  45

Val Ala Val Gly Lys Leu Leu Asp Tyr Leu Asn Gln Asp Asp Pro
                50                  55                  60

Asn Thr Tyr His Tyr Val Val Ser Glu Pro Leu Gly Arg Asn Ser
                65                  70                  75

Tyr Lys Glu Arg Tyr Leu Phe Leu Phe Arg Pro Asn Lys Val Ser
                80                  85                  90

Val Leu Asp Thr Tyr Gln Tyr Asp Asp Gly Cys Glu Ser Cys Gly
                95                 100                 105

Asn Asp Ser Phe Ser Arg Glu Pro Ala Val Val Lys Phe Ser Ser
                110                 115                 120

His Ser Thr Lys Val Lys Glu Phe Ala Ile Val Ala Leu His Ser
                125                 130                 135

Ala Pro Ser Asp Ala Val Ala Glu Ile Asn Ser Leu Tyr Asp Val
                140                 145                 150

Tyr Leu Asp Val Gln Gln Lys Trp His Leu Asn Asp Val Met Leu
                155                 160                 165

Met Gly Asp Phe Asn Ala Asp Cys Ser Tyr Val Thr Ser Ser Gln
                170                 175                 180

Trp Ser Ser Ile Arg Leu Arg Thr Ser Ser Thr Phe Gln Trp Leu
                185                 190                 195

Ile Pro Asp Ser Ala Asp Thr Thr Ala Thr Ser Thr Asn Cys Ala
                200                 205                 210

Tyr Asp Arg Ile Val Val Ala Gly Ser Leu Leu Gln Ser Ser Val
                215                 220                 225

Val Gly Pro Ser Ala Ala Pro Phe Asp Phe Gln Ala Ala Tyr Gly
                230                 235                 240

Leu Ser Asn Glu Met Ala Leu Ala Ile Ser Asp His Tyr Pro Val
                245                 250                 255

Glu Val Thr Leu Thr
                260

(2) INFORMATION FOR SEQ ID NO: 16:

(i) SEQUENCE CHARACTERISTICS:
```

(A) LENGTH: 664 base pairs
        (B) TYPE: Nucleic Acid
        (C) STRANDEDNESS: Double
        (D) TOPOLOGY: Linear (xi) SEQUENCE DESCRIPTION: SEQ ID NO: 16:

| | | |
|---|---|---|
| TTCGAGCTCG CCCGACATTG ATTATTGACT AGAGTCGACA GCTGTGGAAT | | 50 |
| GTGTGTCAGT TAGGGTGTGG AAAGTCCCCA GGCTCCCCAG CAGGCAGAAG | | 100 |
| TATGCAAAGC ATGCATCTCA ATTAGTCAGC AACCAGGTGT GGAAAGTCCC | | 150 |
| CAGGCTCCCC AGCAGGCAGA AGTATGCAAA GCATGCATCT CAATTAGTCA | | 200 |
| GCAACCATAG TCCCGCCCCT AACTCCGCCC ATCCCGCCCC TAACTCCGCC | | 250 |
| CAGTTCCGCC CATTCTCCGC CCCATGGCTG ACTAATTTTT TTTATTTATG | | 300 |
| CAGAGGCCGA GGCCGCCTCG GCCTCTGAGC TATTCCAGAA GTAGTGAGGA | | 350 |
| GGCTTTTTTG GAGGCCTAGG CTTTTGCAAA AAGCTTATCG GCCGGGAAC  | | 400 |
| GGTGCATTGG AACGCGGATT CCCCGTGCCA AGAGTGACGT AAGTACCGCC | | 450 |
| TATAGAGTCT ATAGGCCCAC CCCCTTGGCT TCGTTAGAAC GCGGCTACAA | | 500 |
| TTAATACATA ACCTTATGTA TCATACACAT ACGATTTAGG TGACACTATA | | 550 |
| GAATAACATC CACTTTGCCT TTCTCTCCAC AGGTGTCCAC TCCCAGGTCC | | 600 |
| AACTGCACCT CGGTTCTAAG CTTGGGCTGC AGGTCGCCGT GAATTTAAGG | | 650 |
| GACGCTGTGA AGCA | | 664 |

(2) INFORMATION FOR SEQ ID NO: 17:

(i) SEQUENCE CHARACTERISTICS:
        (A) LENGTH: 664 base pairs
        (B) TYPE: Nucleic Acid
        (C) STRANDEDNESS: Double
        (D) TOPOLOGY: Linear (xi) SEQUENCE DESCRIPTION: SEQ ID NO: 17:

| | | |
|---|---|---|
| TTCGAGCTCG CCCGACATTG ATTATTGACT AGAGTCGACA GCTGTGGAAT | | 50 |
| GTGTGTCAGT TAGGGTGTGG AAAGTCCCCA GGCTCCCCAG CAGGCAGAAG | | 100 |
| TATGCAAAGC ATGCATCTCA ATTAGTCAGC AACCAGGTGT GGAAAGTCCC | | 150 |
| CAGGCTCCCC AGCAGGCAGA AGTATGCAAA GCATGCATCT CAATTAGTCA | | 200 |
| GCAACCATAG TCCCGCCCCT AACTCCGCCC ATCCCGCCCC TAACTCCGCC | | 250 |
| CAGTTCCGCC CATTCTCCGC CCCATGGCTG ACTAATTTTT TTTATTTATG | | 300 |
| CAGAGGCCGA GGCCGCCTCG GCCTCTGAGC TATTCCAGAA GTAGTGAGGA | | 350 |
| GGCTTTTTTG GAGGCCTAGG CTTTTGCAAA AAGCTTATCC GGCCGGGAAC | | 400 |
| GGTGCATTGG AACGCGGATT CCCCGTGCCA AGAGTCAGGT AAGTACCGCC | | 450 |
| TATAGAGTCT ATAGGCCCAC CCCCTTGGCT TCGTTAGAAC GCGGCTACAA | | 500 |
| TTAATACATA ACCTTATGTA TCATACACAT ACGATTTAGG TGACACTATA | | 550 |
| GAATAACATC CACTTTGCCT TTCTCTCCAC AGGTGTCCAC TCCCAGGTCC | | 600 |
| AACTGCACCT CGGTTCTAAG CTTGGGCTGC AGGTCGCCGT GAATTTAAGG | | 650 |
| GACGCTGTGA AGCA | | 664 |

(2) INFORMATION FOR SEQ ID NO: 18:

(i) SEQUENCE CHARACTERISTICS:
        (A) LENGTH: 640 base pairs (B) TYPE: Nucleic Acid
(C) STRANDEDNESS: Double
(D) TOPOLOGY: Linear (xi) SEQUENCE DESCRIPTION: SEQ ID NO: 18:

| | |
|---|---|
| TTCGAGCTCG CCCGACATTG ATTATTGACT AGAGTCGACA GCTGTGGAAT | 50 |
| GTGTGTCAGT TAGGGTGTGG AAAGTCCCCA GGCTCCCCAG CAGGCAGAAG | 100 |
| TATGCAAAGC ATGCATCTCA ATTAGTCAGC AACCAGGTGT GGAAAGTCCC | 150 |
| CAGGCTCCCC AGCAGGCAGA AGTATGCAAA GCATGCATCT CAATTAGTCA | 200 |
| GCAACCATAG TCCCGCCCCT AACTCCGCCC ATCCCGCCCC TAACTCCGCC | 250 |
| CAGTTCCGCC CATTCTCCGC CCCATGGCTG ACTAATTTTT TTTATTTATG | 300 |
| CAGAGGCCGA GGCCGCCTCG GCCTCTGAGC TATTCCAGAA GTAGTGAGGA | 350 |
| GGCTTTTTTG GAGGCCTAGG CTTTTGCAAA AAGCTTATCC GGCCGGGAAC | 400 |
| GGTGCATTGG AACGCGGATT CCCCGTGCCA AGAGTCAGGT AAGTACCGCC | 450 |
| TATAGAGTCT ATAGGCCCAC CCCCTTGGCT TCGTTAGAAC GCGGCTACAA | 500 |
| TTAATACATA ACCTTTTGGA TCCTATAGAC TGACATCCAC TTTGCCTTTC | 550 |
| TCTCCACAGG TGTCCACTCC CAGGTCCAAC TGCACCTCGG TTCGAAGCTT | 600 |
| GGGCTGCAGG TCGCCGTGAA TTTAAGGGAC GCTGTGAAGC | 640 |

(2) INFORMATION FOR SEQ ID NO: 19:

(i) SEQUENCE CHARACTERISTICS:
      (A) LENGTH: 646 base pairs
      (B) TYPE: Nucleic Acid
      (C) STRANDEDNESS: Double
      (D) TOPOLOGY: Linear (xi) SEQUENCE DESCRIPTION: SEQ ID NO: 19:

| | |
|---|---|
| TTCGAGCTCG CCCGACATTG ATTATTGACT AGAGTCGACA GCTGTGGAAT | 50 |
| GTGTGTCAGT TAGGGTGTGG AAAGTCCCCA GGCTCCCCAG CAGGCAGAAG | 100 |
| TATGCAAAGC ATGCATCTCA ATTAGTCAGC AACCAGGTGT GGAAAGTCCC | 150 |
| CAGGCTCCCC AGCAGGCAGA AGTATGCAAA GCATGCATCT CAATTAGTCA | 200 |
| GCAACCATAG TCCCGCCCCT AACTCCGCCC ATCCCGCCCC TAACTCCGCC | 250 |
| CAGTTCCGCC CATTCTCCGC CCCATGGCTG ACTAATTTTT TTTATTTATG | 300 |
| CAGAGGCCGA GGCCGCCTCG GCCTCTGAGC TATTCCAGAA GTAGTGAGGA | 350 |
| GGCTTTTTTG GAGGCCTAGG CTTTTGCAAA AAGCTTATCC GGCCGGGAAC | 400 |
| GGTGCATTGG AACGCGGATT CCCCGTGCCA AGAGTCAGGT AAGTACCGCC | 450 |
| TATAGAGTCT ATAGGCCCAC CCCCTTGGCT TCGTTAGAAC GCGGCTACAA | 500 |
| TTAATACATA ACCTTTTGGA TCCTACTAAC TACTGACTTA TTCTTTTCCT | 550 |
| TTCTCTCCAC AGGTGTCCAC TCCCAGGTCC AACTGCACCT CGGTTCGCGA | 600 |
| AGCTTGGGCT GCAGGTCGCC GTGAATTTAA GGGACGCTGT GAAGCA | 646 |

(2) INFORMATION FOR SEQ ID NO: 20:

(i) SEQUENCE CHARACTERISTICS:
      (A) LENGTH: 645 base pairs
      (B) TYPE: Nucleic Acid
      (C) STRANDEDNESS: Double
      (D) TOPOLOGY: Linear (xi) SEQUENCE DESCRIPTION: SEQ ID NO: 20:

```
TTCGAGCTCG CCCGACATTG ATTATTGACT AGAGTCGACA GCTGTGGAAT        50

GTGTGTCAGT TAGGGTGTGG AAAGTCCCCA GGCTCCCCAG CAGGCAGAAG       100

TATGCAAAGC ATGCATCTCA ATTAGTCAGC AACCAGGTGT GGAAAGTCCC       150

CAGGCTCCCC AGCAGGCAGA AGTATGCAAA GCATGCATCT CAATTAGTCA       200

GCAACCATAG TCCCGCCCCT AACTCCGCCC ATCCCGCCCC TAACTCCGCC       250

CAGTTCCGCC CATTCTCCGC CCCATGGCTG ACTAATTTTT TTTATTTATG       300

CAGAGGCCGA GGCCGCCTCG GCCTCTGAGC TATTCCAGAA GTAGTGAGGA       350

GGCTTTTTTG GAGGCCTAGG CTTTTGCAAA AAGCTTATCC GGCCGGGAAC       400

GGTGCATTGG AACGCGGATT CCCCGTGCCA AGAGTCAGGT AAGTACCGCC       450

TATAGAGTCT ATAGGCCCAC CCCCTTGGCT TCGTTAGAAC GCGGCTACAA       500

TTAATACATA ACCTTTTGGA TCCTACTGAC ACTGACATCC ACTTTTTCTT       550

TTTCTCCACA GGTGTCCACT CCCAGGTCCA ACTGCACCTC GGTTCGCGAA       600

GCTTGGGCTG CAGGTCGCCG TGAATTTAAG GGACGCTGTG AAGCA           645

(2) INFORMATION FOR SEQ ID NO: 21:

(i) SEQUENCE CHARACTERISTICS:
        (A) LENGTH: 81 base pairs
        (B) TYPE: Nucleic Acid
        (C) STRANDEDNESS: Single
        (D) TOPOLOGY: Linear (xi) SEQUENCE DESCRIPTION: SEQ ID NO: 21:

TGACGTAAGT ACATGTATCA TACACATACG ATTTAGGTGA CACTATAGAA        50

TAACATCCAC TTTGCCTTTC TCTCCACAGG T                           81

(2) INFORMATION FOR SEQ ID NO: 22:

(i) SEQUENCE CHARACTERISTICS:
        (A) LENGTH: 81 base pairs
        (B) TYPE: Nucleic Acid
        (C) STRANDEDNESS: Single
        (D) TOPOLOGY: Linear (xi) SEQUENCE DESCRIPTION: SEQ ID NO: 22:

TCAGGTAAGT ACATGTATCA TACACATACG ATTTAGGTGA CACTATAGAA        50

TAACATCCAC TTTGCCTTTC TCTCCACAGG T                           81

(2) INFORMATION FOR SEQ ID NO: 23:

(i) SEQUENCE CHARACTERISTICS:
        (A) LENGTH: 58 base pairs
        (B) TYPE: Nucleic Acid
        (C) STRANDEDNESS: Single
        (D) TOPOLOGY: Linear (xi) SEQUENCE DESCRIPTION: SEQ ID NO: 23:

TCAGGTAAGT ACTTGGATCC TATAGACTGA CATCCACTTT GCCTTTCTCT        50

CCACAGGT                                                     58

(2) INFORMATION FOR SEQ ID NO: 24:

(i) SEQUENCE CHARACTERISTICS:
        (A) LENGTH: 61 base pairs
        (B) TYPE: Nucleic Acid
        (C) STRANDEDNESS: Single
```

-continued

```
        (D) TOPOLOGY: Linear (xi) SEQUENCE DESCRIPTION: SEQ ID NO: 24:

TCAGGTAAGT ACTTGGATCC TACTAACTAC TGACTTATTC TTTTCCTTTC        50

TCTCCACAGG T                                                  61

(2) INFORMATION FOR SEQ ID NO: 25:

(i) SEQUENCE CHARACTERISTICS:
        (A) LENGTH: 60 base pairs
        (B) TYPE: Nucleic Acid
        (C) STRANDEDNESS: Single
        (D) TOPOLOGY: Linear (xi) SEQUENCE DESCRIPTION: SEQ ID NO: 25:

TCAGGTAAGT ACTTGGATCC TACTGACACT GACATCCACT TTTTCTTTTT        50

CTCCACAGGT                                                    60
```